United States Patent
Power et al.

(10) Patent No.: US 9,803,181 B2
(45) Date of Patent: *Oct. 31, 2017

(54) HYBRID ALPHA-AMYLASES

(71) Applicant: Danisco US Inc., Palo Alto, CA (US)

(72) Inventors: Scott D. Power, San Bruno, CA (US); Andrew Shaw, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/340,856

(22) Filed: Jul. 25, 2014

(65) Prior Publication Data
US 2015/0017701 A1    Jan. 15, 2015

Related U.S. Application Data

(62) Division of application No. 13/132,881, filed as application No. PCT/US2009/067639 on Dec. 11, 2009, now Pat. No. 8,841,107.

(60) Provisional application No. 61/122,628, filed on Dec. 15, 2008.

(51) Int. Cl.
*C12N 9/28* (2006.01)
*G06F 19/12* (2011.01)
*G06F 19/16* (2011.01)

(52) U.S. Cl.
CPC ......... *C12N 9/2417* (2013.01); *G06F 19/12* (2013.01); *G06F 19/16* (2013.01); *C07K 2319/00* (2013.01)

(58) Field of Classification Search
CPC ............ C12N 9/28; G06F 19/12; G06F 19/16
See application file for complete search history.

(56) References Cited

U.S. PATENT DOCUMENTS

| 5,874,276 A | 2/1999 | Fowler et al. |
| 6,022,725 A | 2/2000 | Fowler et al. |
| 6,143,708 A | 11/2000 | Svendsen et al. |

(Continued)

FOREIGN PATENT DOCUMENTS

| EP | 215594 | 3/1987 |
| EP | 244234 | 4/1987 |

(Continued)

OTHER PUBLICATIONS

GenBank AAM48114, Ultrathin (May 5, 2004).*

(Continued)

*Primary Examiner* — Alexander Kim
(74) *Attorney, Agent, or Firm* — Danisco US Inc.

(57) ABSTRACT

Hybrid alpha-amylases are provided that share a conserved 3D structure in whole or in part with a wild-type Termamyl-like α-amylase, e.g., a *Bacillus* amylase. In the hybrid, an N-terminal portion of a Termamyl-like α-amylase is replaced with sequences from an archae α-amylase. The sequence similarity between the two amylase sequences may be less than 60%. Conserving the wild-type 3D structure in the hybrid facilitates obtaining enzymatically active amylases. In one embodiment, one or both amylase sequences contribute residues to the B domain, resulting in particularly advantageous properties. For instance, replacement of the $Ca^{2+}$ binding site in the B domain of the Termamyl-like α-amylase with a B domain sequence of an archae α-amylase that does not bind $Ca^{2+}$ can produce a hybrid that is fully active in the absence of $Ca^{2+}$.

5 Claims, 7 Drawing Sheets

(56) References Cited

U.S. PATENT DOCUMENTS

| | | | |
|---|---|---|---|
| 6,268,328 | B1 | 7/2001 | Mitchinson et al. |
| 6,667,065 | B1 | 12/2003 | Kragh et al. |
| 6,890,572 | B2 | 5/2005 | Kragh et al. |
| 7,166,453 | B2 | 1/2007 | Kragh et al. |
| 7,541,026 | B2 | 6/2009 | Power et al. |
| 7,749,744 | B2 | 7/2010 | Borchert et al. |
| 8,153,412 | B2 | 4/2012 | Chang et al. |
| 8,323,945 | B2 | 12/2012 | Cascao-Pereira et al. |
| 8,507,244 | B2 | 8/2013 | Shaw et al. |

FOREIGN PATENT DOCUMENTS

| | | |
|---|---|---|
| WO | WO96/23874 | 8/1996 |
| WO | WO97/41213 | 11/1997 |
| WO | WO00/60059 | 10/2000 |
| WO | WO2010/074999 | 7/2010 |

OTHER PUBLICATIONS

Richardson et al., A novel, high performance enzyme for starch liquefaction. Discovery and optimization of a low pH, thermostable alpha-amylase., J Biol Chem. 2002, vol. 277(29), pp. 26501-26507.*
BD5088 (CAV13408.1) Dec. 16, 2008.*
Conrad et al., Hybrid Bacillus amyloliquefaciens X Bacillus licheniformis alpha-amylases. Construction, properties and sequence determinants., Eur J Biochem. (1995), vol. 230(2), pp. 481-490.*
Guo et al., Protein tolerance to random amino acid change, (2004) Proc. Natl. Acad. Sci. USA 101: 9205-9210.*
Lazar et al., Trnasforming Growth Factor alpha: Mutation of aspartic Acid 47 and Leucine 48 Results in Different Biological Activities, (1988) Mol. Cell. Biol. 8:1247-1252.*
Hill et al., Functional Analysis of Conserved Histidines in ADP-Glucose Pyrophosphorylase from *Escherichia coli*, (1998) Biochem. Biophys. Res. Comm. 244:573-577.*
Brzozowski, et al., "Structural Analysis of a Chimeric Bacterial α-Amylase. High-Resolution Analysis of Native and Ligand Complexes." Biochemistry 39: 9099-9107, 2000.
Campbell, et at., "Improved transformation efficiency of Aspergillus niger using the homologous niaD gene for nitrate reductase", Curr Genet, (1989), 16:53-6.
Conrad, et al., "Hybrid Bacillus amyloliquefaciens X Bacillus licheniformis alpha-amylases. Construction, properties and sequence determinants", Eur J Biochem, (1995), 230:481-90.
Ferrari, et al., "Construction and properties of an integrable plasmid for Bacillus subtilis", J Bacteriol, (1983), 154:1513-5.
Gray, et al., "Structural genes encoding the thermophilic alpha-amylases of Bacillus stearothermophilus and Bacillus licheniformis." J. Bacteriol. 166(2): 635-643, 1986.
Harkki, et al., "A novel fungal expression system: secretion of active calf chymosin from the filamentous fungus trichoderma reesei", Nature Biotechnol, (1989), 7:596-603.
Harkki, et al., "Genetic engineering of Trichoderma to produce strains with novel cellulase profiles", Enzyme Microb Technol, (1991), 13:227-33.
International Search Report and the Written Opinion of the International Searching Authority for International Application No. PCT/US2009/067639 dated Mar. 18, 2010.
Janecek, et al., "Close evolutionary relatedness of alpha-amylases from Archaea and plants", J Mol Evol, (1999), 48:421-6.
Kelly, et al., "Transformation of Aspergillus niger by the amdS gene of Aspergillus nidulans", EMBO J, (1985), 4:475-9.
Leveque, et al: "Thermophilic Archaeal Amylolytic Enzymes." Enzyme and Microbial Technology 26(1): 3-14, 2000.
Linden, A., et al., "Differential Regualtion of a Hyperthermophilic α-Amylase with a Novel (Ca,Zn) Two-metal Center by Zinc." *J. Biol. Chem.* 278(11): 9875-9884-, 2003.

Lolis, et al., "Structure of Yeast Triosephosphate Isomerase at 1.9-Å Resolution." Biochemistry 29: 6609-6618, 1990.
Orengo, et al., "Identification and classification of protein fold families", Protein Eng, (1993), 6:485-500.
Penttila, et al., "A versatile transformation system for the cellulolytic filamentous fungus Trichoderma reesei", Gene, (1987), 61:155-64.
Richardson, et al., "A novel, high performance enzyme for starch liquefaction. Discovery and optimization of a low pH, thermostable α-amylase." J. Biological Chemistry 277(29): 26501-26507, 2002.
Svensson, B., "Protein Engineering in the α-Amylase Family: Catalytic Mechanism, Substrate Specificity, and Stability." Plant Molecular Biology 25: 141-157, 1994.
Thompson, et al., "CLUSTAL W: improving the sensitivity of progressive multiple sequence alignment through sequence weighting, position-specific gap penalties and weight matrix choice", Nucleic Acids Res, (1994), 22:4673-80.
Van Den Hondel, et al., "More Gene Manipulations in Fungi; Heterologous gene expression in filamentous fungi", TNO Medical Biol Lab, (1991), 18:396-428.
Accession AAM48115.1, Richardson, T.H. et al., "alpha-amylase precursor", (2002), 1 pg., http://www.ncbi.nlm.nih.gov/protein/AAM48115.1.
Accession No. 1HVX, Suvd, et al., "Bacillus Stearothermophilus Alpha-Amylase", (2001), http://www.rcsb.org/pdb/files/1HVX.pdb.
Accession No. 1MXG, Linden, et al., "Crystal Strucutre of a (Ca,Zn)-Dependent Alpha-Amylase from the Hyperthermophilic Archaeon Pyrococcus Woesei in Complex With Acarbose", (2002), http://www.rcsb.org/pdb/files/1MXG.pdb.
Notice of Opposition as filed on Jun. 17, 2015 in the European Patent Office against European Patent No. EP 2 358 873; filed by Maiwald Patentanwalts GmbH on behalf of BASF SE.
Reply of the patent proprietor to the Notice of Opposition as filed on Feb. 8, 2016 in the European Patent Office in support of European Patent No. EP 2 358 873; filed by Mewburn Ellis on behalf of Danisco US Inc.
European Patent Office Communication dated Jun. 27, 2016; Summons to attend oral proceedings pursuant to Rule 115(1) EPC.
Amino acid sequence alignment of BD5088 disclosed in document 02 with SEQ ID No. 9 of the patent-in-suit (Opponent's Reference No. D2a as cited in the European Opposition of EP2358873).
Wikipedia excerpt for Pyrococcus woesei (Opponent's Reference No. D2b as cited in the European Opposition of EP2358873).
Wikipedia excerpt for Thermococcus (Opponent's Reference No. D2c as cited in the European Opposition of EP2358873).
Applicant's submission dated Nov. 12, 2012 as submitted in European Patent Application No. 09 768 480.7 (Opponent's Reference No. D4 as cited in the European Opposition of EP2358873).
Result of the alignment of the 30 structures of the Ultrathin α-amylase and the α-amylase from Bacillus stearothermophilus(Opponent's Reference No. D7 as cited in the European Opposition of EP2358873).
Table summarizing root mean square distances of amino acids x and y in hybrids A to H according to the patent as determined in document D7 (Opponent's Reference No. D8 as cited in the European Opposition of EP2358873).
Result of the alignment of the 30 structures of the a-amylases from Pyrococcus woesei and Bacillus stearothermophilus (Opponent's Reference No. D9 as cited in the European Opposition of EP2358873).
Table summarizing alignments of 30 structures (Opponent's Reference No. D10 as cited in the European Opposition of EP2358873).
Result of the alignment of the 30 structures of the a-amylases from Pyrococcus woesei and Bacillus halmapalus (Opponent's Reference No. D11 as cited in the European Opposition of EP2358873).
Result of the alignment of the 30 structures of the a-amylases from Pyrococcus woesei and Bacillus licheniformis (Opponent's Reference No. D12 as cited in the European Opposition of EP2358873).
Result of the alignment of the 30 structures of the a-amylases from *Pyrococcus woesei* and B. sp. KSM-K38 (Opponent's Reference No. D13 as cited in the European Opposition of EP2358873).

(56) References Cited

OTHER PUBLICATIONS

Result of the alignment of the 30 structures of the a-amylases from Pyrococcus woesei and Bacillus subtilis (Opponent's Reference No. D14 as cited in the European Opposition of EP2358873).

European Patent Office Communication, Interlocutory Decision in Opposition Proceedings (Art. 101(3)(a) and 106(2) EPC), for European Patent No. EP2358873, dated Apr. 12, 2017, 70 pages.

Citation D15, "Alignment Match 1 of 1," submitted on Jan. 9, 2017, in Opposition Procedure for European Patent No. EP2358873, *EMBL-EBI*, 2016, http://www.cbi.ac.uk/msd-srv.ssm/cgi-bin/ssmserver, [Dec. 20, 2016 10:55:59].

Citation D16, "Identification of Amino Acids Meeting the RMSD Criterion," submitted on Jan. 9, 2017, in Opposition Procedure for European Patent No. EP2358873, 1 page.

Citation D17, "RMSD Determined with the MOE Algorithm," submitted on Jan. 9, 2017, in Opposition Procedure for European Patent No. EP2358873, 9 pages.

Citation D18, "Table of Activities and RMSD for Hybrids A-H," submitted on Jan. 9, 2017, in Opposition Procedure for European Patent No. EP2358873, 1 page.

Citation D19, "RMSD for Hybrids A-H Compared to AmyS," submitted on Jan. 9, 2017, in Opposition Procedure for European Patent No. EP2358873, 2 pageS.

Citation D20, "RMSD for Yybrids A-H Compared to AmyS Using two Different Programs," in Opposition Procedure for European Patent No. EP2358873, 1 page.

\* cited by examiner

FIG. 1

```
                    1                                               50
MatAmyS       (1)  ----AAPFNGTMMQYFEWYLPDDGTLWTKVANEANNLSSLGITALWLPPA
MatUltrathin  (1)  AKYSELEKGGVIMQAFYWDVPSGGIWWDTIRQKIPEWYDAGISAIWIPPA
Consensus     (1)          G IMQ F W LP G  W   I N       GISAIWIPPA 51                                              100
MatAmyS       (47) YKGTS-RSDVGYGVYILYDLGEFNQKGTVRTKYGTKAQYLQAIQAAHAAG
MatUltrathin  (51) SKGMGGAYSMGYDPYDFFDLGEYDQKGTVETRFGSKQELVNMINTAHAYG
Consensus     (51) KG     MGY Y  FDLGEF QKGTV TK GSK   LN IN AHA G 101                                             150
MatAmyS       (96) MQVYADVVFDHKGGADGTEWVDAVEVNPSDRNQEISGTYQIQAWTKFDFP
MatUltrathin  (101) MKVIADIVINHRAGGDLEWNPFVNDYTWTDFSKVASGKYTANYLDFHPNE
Consensus     (101) M V ADIV  HKAGAD  D       SD    SG Y N 151                                             200
MatAmyS       (146) GRGNTYSSFKWRWYHFDGVDWDESRKLSRIYKFRGIGKAWDWEVDTENGN
MatUltrathin  (151) LHAGDSGTFGGYPDICRDKSWDQY---------------WLWASQES---
Consensus     (151)      A   SF          WD                   W W 201                                             250
MatAmyS       (196) YDYLMYADLDMDHPEVVTELKSWGKWYVNTTNIDGFRLDAVKHIKFSFFP
MatUltrathin  (183) ----------------------YAAYLRSIGIDAWRFDYVKGYAPWVVK
Consensus     (201)                       YL S  IDAFR D VK 251                                             300
MatAmyS       (246) DWLSYVRSQTGKPLFTVGEYWSYDINKLHNYIMKTNGTMSLFDAPLHNKF
MatUltrathin  (210) DWLNWWG------GWAVGEYWDTNVDAVLNWAYSSG--AKVFDFALYYKM
Consensus     (251) DWL W        F VGEYW    I  L NW   S     LFD  L  K 301                                             350
MatAmyS       (296) YTASKSGGTFDMRTLMTN--TLMKDQPTLAVTFVDNHDTEPGQALQSWVD
MatUltrathin  (252) DEAFDNKNIPALVSALQNGQTVVSRDPFKAVTFVANHDTD--------I
Consensus     (301)   A        L S L N  T  M   P  AVTFV NHDTD 351                                             400
MatAmyS       (344) PWFKPLAYAFILTRQEGYPCVFYGDYYGIPQYNIPSLKSKIDPLLIARRD
MatUltrathin  (293) IWNKYPAYAFILTYE-GQPTIFYRDYEEWLN------KDKLKNLIWIHEN
Consensus     (351)  W K  AYAFILT   G P  IFY DY    N      K KL LI 401                                             450
MatAmyS       (394) YAYGTQHDYLDHSDIIGWTREGVTEKPCSCLAALITDGPG-GSKWMYVGK
MatUltrathin  (336) LAGGSTDIVYYDNDELIFVRNGYGDKPG--LITYINLGSSKAGRWVYVF-
Consensus     (401)  A GS     D    I  F R G  DKPG   L  I  G  A KWMYV 451                                             500
MatAmyS       (443) QHAGKVFYDLTGNRSDTVTINSDGWEFKVNGGSVSVWVPRKTTVSTIAR
MatUltrathin  (383) KFAGACIHEYTGN---------------LGGWVDKYVYSSGWVYLEAP
Consensus     (451)   AG   HD TGN                 GG V  WV  V   A 501           523
MatAmyS       (493) PITTRPWTGEFVRWTEPRLVANF
MatUltrathin  (416) AYDPANGQYGYSVWSYCGVG---
Consensus     (501)         F    WS   L
```

FIG. 2
Panel A
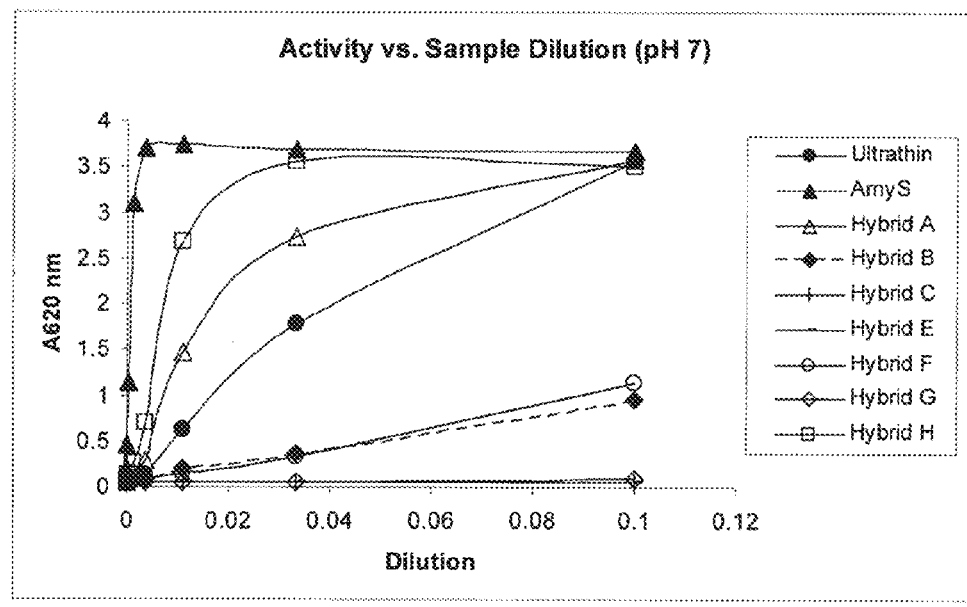
Panel B
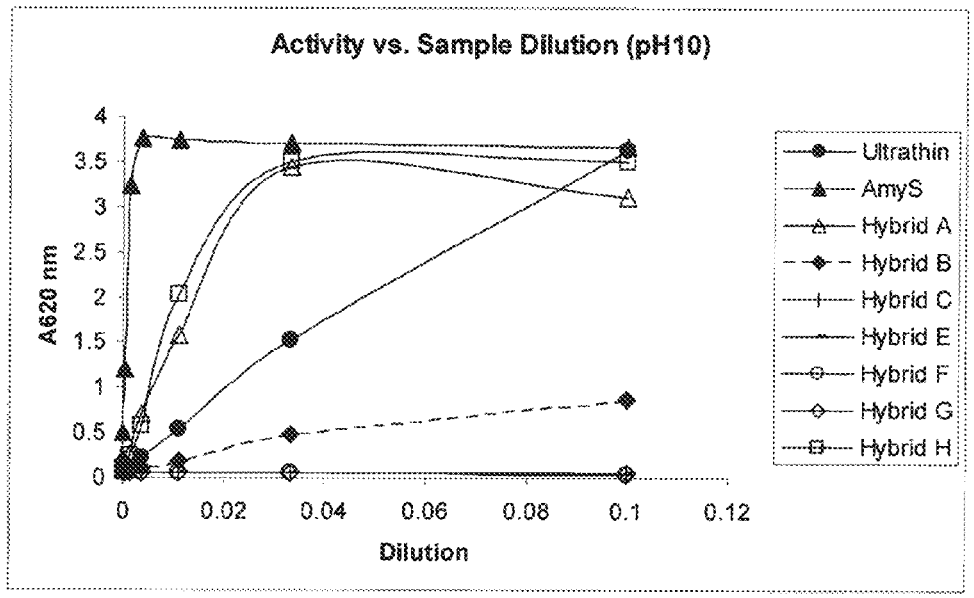

FIG. 3

```
         10         20         30         40         50
60
AKYSELEKGG VIMQAFYWDV PSGGIWWDTI RQKIPEWYDA GISAIWIPPA
SKGMGGAYSM 70         80         90        100        110
120
GYDPYDFFDL GEYDQKGTVE TRFGSKQELV NMINTAHAYG MKVIADIVIN
HRAGGDLEWN 130        140        150        160        170
180
PFVNDYTWTD FSKVASGKYT ANYLDFHPNE LHAGDSGTFG GYPDICHDKS
WDQYWLWASQ 190        200        210        220        230
240
ESYAAYLRSI GIDAWRFDYV KGYAPWVVKD WLNWWGGWAV GEYWDTNVDA
VLNWAYSSGA 250        260        270        280        290
300
KVPDFALYYK MDEAFDNKNI PALVSALQNG QTVVSRDPFK AVTFVANHDT
DIIWNKYPAY 310        320        330        340        350
360
AFILTYEGQP TIFYRDYEEW LNKDKLKNLI WIHENLAGGS TDIVYYDNDE
LIFVRNGYGD 370        380        390        400        410
420
KPGLITYINL GSSKAGRWVY VPKFAGACIH EYTGNLGGWV DKYVYSSGWV
YLEAPAYDPA

430
NGQYGYSVWS YCGVG
```

FIG. 4

```
         10         20         30         40         50
 60
AAPFNGTMMQ YFEWYLPDDG TLWTKVANEA NNLSSLGITA LWLPPAYKGT
SRSDVGYGVY 70         80         90        100        110
120
DLYDLGEFNQ KGTVRTKYGT KAQYLQAIQA AHAAGMQVYA DVVFDHKGGA
DGTEWVDAVE 130        140        150        160        170
180
VNPSDRNQEI SGTYQIQAWT KFDFPGRGNT YSSFKWRWYH FDGVDWDESR
KLSRIYKFRG 190        200        210        220        230
240
IGKAWDWEVD TENGNYDYLM YADLDMDHPE VVTELKNWGK WYVNTTNIDG
FRLDAVKHIK 250        260        270        280        290
300
FSFFPDWLSY VRSQTGKPLF TVGEYWSYDI NKLHNYITKT NGTMSLFDAP
LHNKFYTASK 310        320        330        340        350
360
SGGAFDMRTL MTNTLMKDQP TLAVTFVDNH DTEPGQALQS WVDPWFKPLA
YAFILTRQEG 370        380        390        400        410
420
YPCVFYGDYY GIPQYNIPSL KSKIDPLLIA RRDYAYGTQH DYLDHSDIIG
WTREGVTEKP 430        440        450        460        470
480
GSGLAALITD GPGGSKWMYV GKQHAGKVFY DLTGNRSDTV TINSDGWGEF
KVNGGSVSVW

VPRKTT
```

FIG. 5B
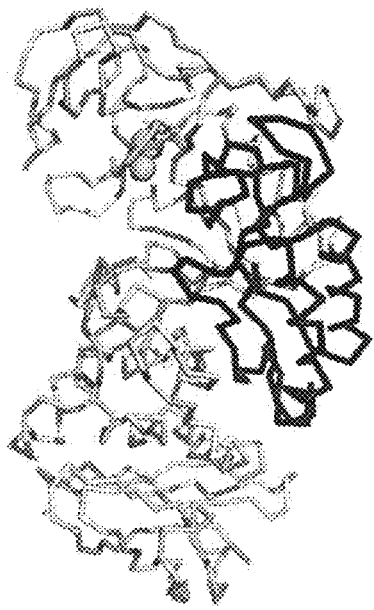
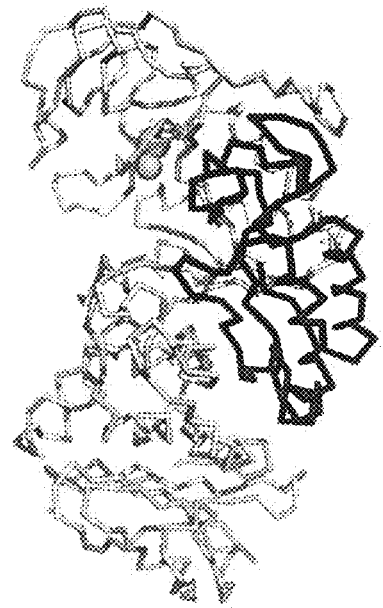
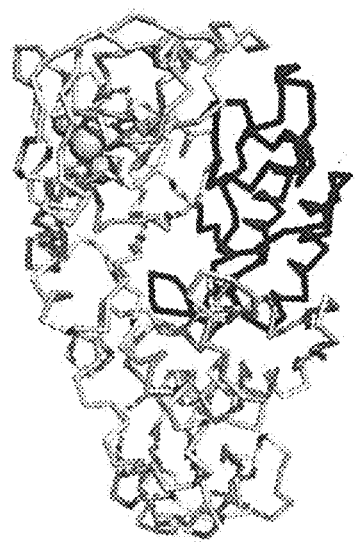
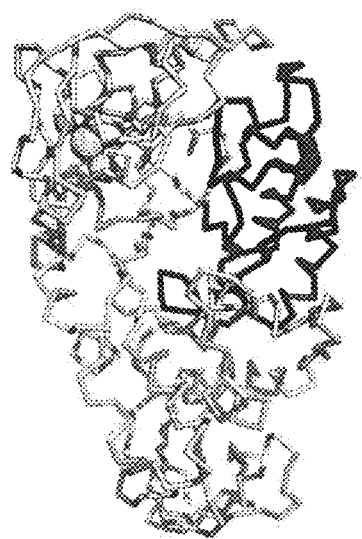

FIG. 5C
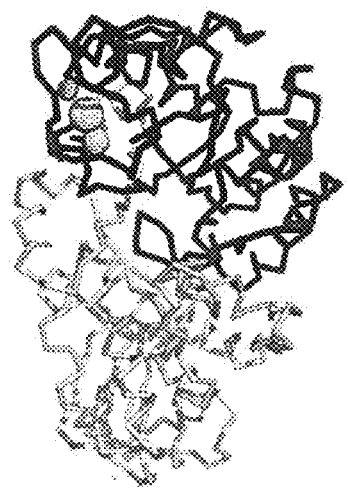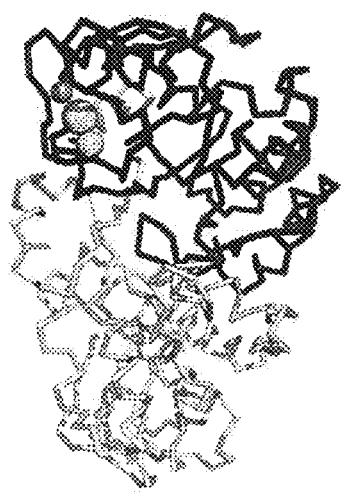
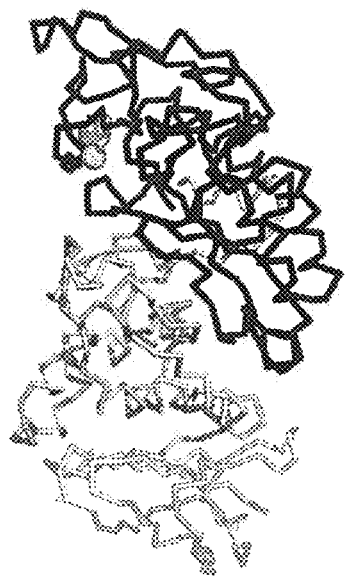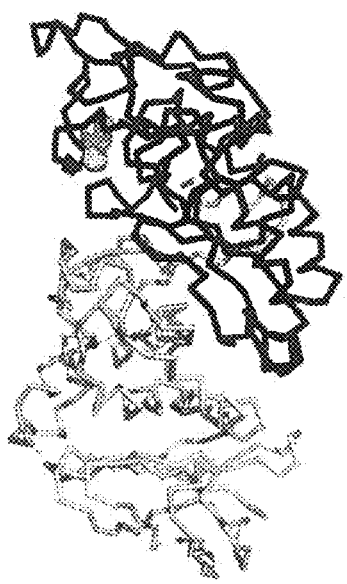

HYBRID ALPHA-AMYLASES

PRIORITY

The present application is a divisional of U.S. patent application Ser. No. 13/132,881, filed Sept. 21, 2011, now U.S. Pat. No. 8,841,107, which is a U.S. National Stage application of International Application No. PCT/US2009/067639, filed Dec. 11, 2009, which claims priority to U.S. Provisional Application Serial. No. 61/122,628filed Dec. 15, 2008, all of which are hereby incorporated by reference in their entireties.

SEQUENCE LISTING

A Sequence Listing, comprising SEQ ID NOS: 1-27, is attached and is incorporated by reference in its entirety.

FIELD OF THE INVENTION

Hybrid amylases comprising archae α-amylase and Termamyl-like α-amylase sequences are provided. The hybrid amylases may have altered properties, compared to the wild-type Termamyl-like α-amylase.

BACKGROUND

Related enzymes that have a common function may or may not have significant sequence identity. For example, Bacillus alpha-amylases (1,4-α-D-glucan glucanohydrolase, EC 3.2.1.1) are classified as "Termamyl-like" if their amino acid sequences share 60% or higher identity to B. licheniformis alpha-amylase. See WO 96/23874. Hybrid amylases can be created between amylases sharing 62% or higher sequence identity. See Gray et al., J. Bacteriology 166: 635-43 (1986); U.S. Pat. No. 6,143,708. For example, a chimeric amylase containing residues 1-300 of Bacillus amyloliquefaciens and residues 301-483 of B. licheniformis has been recombinantly expressed and crystallized. See Brzozowski et al., Biochemistry 39: 9099-107 (2000); see also WO 96/23874; WO 97/41213. However, even amylases sharing less than 25% sequence identity, such as the amylases from Bacillus subtilis and B. licheniformis, nevertheless may share a common catalytic function and an overall conserved three-dimensional (3D) fold.

Crystal structures of numerous amylases are currently available. See Brzozowski et al. (2000) supra. The Protein Data Bank (PDB), for example, contains 3D structures of at least the amylases shown in TABLE 1.

TABLE 1

| PDB Acc. No. | Amylase |
| --- | --- |
| 1rp8 | Barley alpha-amylase |
| 1pif | Pig alpha-amylase |
| 1aqm | Alteromonas haloplanctis alpha-amylase |
| 1hvx | Bacillus stearothermophilus alpha-amylase |
| 1ua7 | Bacillus subtilis alpha-amylase |
| 1mxd | Pyrococcus woesei alpha-amylase |
| 1jae | Tenebrio molitor larval alpha-amylase |
| 1wza | Halothermothrix orenii alpha-amylase |
| 1ud2 | Bacillus sp. KSM-K38 alpha-amylase |
| 2guy | Aspergillus niger alpha-amylase |
| 1smd | Human salivary alpha-amylase |
| 1kbb | Human pancreatic alpha-amylase (same as above) |
| 1bli | Bacillus licheniformis alpha-amylase |
| 2gjr | Bacillus halmapalus alpha-amylase |
| 1uh2 | Thermoactinomyces vulgaris R-47 alpha-amylase |

Comparison of these crystal structures reveals a high degree of conservation of three-dimensional (3D) structure, even in the absence of significant sequence similarity. All reported alpha-amylase structures share a $(\beta/\alpha)_8$ catalytic core domain, domain A. "$(\beta/\alpha)_8$" refers to a so-called "TIM barrel structure," defined as a conserved protein 3D conformation, or "fold," consisting of eight α-helices and eight parallel β-strands that alternate along the peptide backbone. See Lolis et al., Biochemistry 29: 6609-18 (1990). The B domain is an excursion, or extended structure, between the barrel strand β-3 and helix α-3 of domain A. The C domain, typically an eight-stranded β-sheet, forms the remaining C-terminal portion of the amylases. The domain structure of amylases is described in more detail below.

There is a continuing need in the art to provide variant alpha-amylases that fold properly, maintain stability, and demonstrate efficient expression in a recombinant host cell, without the necessity of making wholesale changes to the amino acid sequence or 3D structure of the protein.

SUMMARY

The 3D structure of a Termamyl-like alpha-amylase is used as a guide to construct novel hybrid alpha-amylases. In the hybrid amylase, a portion of the N-terminus of a Termamyl-like alpha-amylase is replaced with sequences from an archae amylase. The two amylases share a conserved 3D structure. Further, the sequence identity between the amylases may be less than 60%. In one embodiment, the hybrid amylase contains about 400 to about 500 amino acid residues. Between about 10% and about 80% of the total amino acids in the hybrid amylase are contributed by the archae α-amylase. The replaced portion in the hybrid enzyme is predicted to have a 3D structure that is structurally conserved in whole or in part with the Termamyl-like amylase. In one embodiment, at least the C-terminal residue of the archae amylase sequence (residue "x") and the N-terminal residue of the Termamyl-like amylase sequence (residue "y") are structurally conserved. The hybrid amylase advantageously may combine desirable properties of the constituent amylase sequences, such as an altered level of recombinant expression, altered solubility, and desirable performance properties, such as optimal pH activity profiles, substrate specificity, product characteristics, and specific activity.

Because protein domains are often thought to fold as independent units, it might be expected that domains would have to be replaced as whole units to maintain proper folding in a hybrid enzyme. By designing the hybrids to maintain the conserved fold of the wild-type Bacillus enzyme, however, the alpha-amylase sequences need not be fused at domain boundaries. In some embodiments, a hybrid amylase comprises a first amino acid sequence containing a portion of the B domain from a first alpha-amylase, which is fused to a second amino acid sequence from a Bacillus alpha-amylase containing the remaining portion of the B domain. In this manner, hybrid amylases with unique properties can be designed, depending on the particular portion of the B domains that are fused together.

For example, certain embodiments are directed to hybrid amylases containing sequences from B. stearothermophilus alpha-amylase (AmyS; also known in the art as Geobacillus stearothermophilus) fused to sequences from "Ultrathin," an archae alpha-amylase disclosed in Richardson et al., J. Biol. Chem. 277: 26501-07 (2002) (GenBank™ Accession No. AAM48114). In various embodiments disclosed herein, the N-terminus of the hybrid is composed of amino acid residues from Ultrathin (i.e., the first amino acid sequence), while the C-terminus is composed of residues from AmyS (i.e., the second amino acid sequence). Specific Ultrathin residues are denoted "UT n," where n is the amino acid residue number from the N-terminus. For example, residue 104 of Ultrathin is denoted "UT 104." The term "des-Met Ultrathin" refers to Ultrathin lacking an N-terminal methionine residue. A hybrid amylase between Ultrathin residues 1-104 and AmyS residues 100-483, for example, is denoted "UT 1-104: AmyS 100-483."

Ultrathin, like other archae amylases, has a $Zn^{2+}$ binding site in the B domain. By contrast, the B domain of *Bacillus* alpha-amylases has a $Ca^{2+}$—$Na^+$—$Ca^{2+}$ binding site. A hybrid containing the $Zn^{2+}$ binding site of Ultrathin fused to the remaining B domain from a *Bacillus* alpha-amylase can have performance characteristics of a *Bacillus* alpha-amylase without requiring $Ca^{2+}$ for enzymatic activity. Such a hybrid amylase may be particularly useful when used in combination with another enzyme, such as a glucoamylase, that has a different calcium requirement from a wild-type *Bacillus* alpha-amylase. For example, the hybrid amylase may be used to saccharify starch in the same reaction vessel as a glucoamylase, for example, where the $Ca^{2+}$ concentration can be optimized for performance of the glucoamylase.

Accordingly, the present disclosure provides a hybrid amylase comprising the polypeptide having, from N-terminus to C-terminus, formula (I):

A-x-y-B  (I), wherein A is a first amino acid sequence from an archae alpha-amylase, B is a second amino acid sequence from a wild-type Termamyl-like alpha-amylase or a variant thereof, x is a C-terminal residue of the first amino acid sequence, and y is a N-terminal residue of the second amino acid sequence. The Termamyl-like alpha-amylase variant may have at least about 80%, about 85%, about 90%, about 95%, or about 99% sequence identity to the wild-type Termamyl-like alpha-amylase. The first and second amino acid sequences together may contain about 400, about 410, about 420, about 430, about 440, about 450, about 460, about 470, about 480, about 490, or about 500 amino acid residues. About 10%, about 20%, about 30%, about 40%, about 50%, about 60%, about 70%, or about 80% of amino acids in the hybrid amylase may be contributed by the archae alpha-amylase. Both residues x and y are structurally conserved in the hybrid amylase as compared to the wild-type Termamyl-like alpha-amylase. The hybrid amylase may comprise the amino acid sequence shown in any one of SEQ ID NOs: 1-8. In a further aspect, the hybrid amylase may be purified.

In one aspect, the root mean square distance between alpha carbons in residues x and y compared to the wild-type Termamyl-like alpha-amylase 3D structure is no more than about 0.5 Å, about 0.4 Å, about 0.3 Å, about 0.2 Å, or about 0.1 Å. In another aspect, the first amino acid sequence A is structurally conserved in the hybrid amylase compared to the wild-type Termamyl-like alpha-amylase. The wild-type Termamyl-like alpha-amylase may be a *Bacillus* alpha-amylase. The *Bacillus* alpha-amylase may be a *Bacillus stearothermophilus* alpha-amylase, *B. licheniformis* alpha-amylase, *B. subtilis* alpha-amylase, *Bacillus* sp. KSM-K38 alpha-amylase, or *B. halmapalus* alpha-amylase. The Termamyl-like alpha-amylase variant may derive from the *B. stearothermophilus* alpha-amylase by removing the C-terminus of the parent enzyme. The archae alpha-amylase may be Ultrathin alpha-amylase. The first and second amino acid sequences of the hybrid amylase are derived from amylases that may share less than about 60%, about 55%, about 50%, about 45%, about 40%, about 35%, or about 30% sequence identity. Also contemplated is a hybrid amylase that comprises a $Zn^{2+}$ binding site within its first amino acid sequence. The hybrid amylase may have at least one amino acid of a $Ca^{2+}$ binding site of the wild-type Termamyl-like alpha-amylase replaced with an amino acid residue from the first amino acid sequence.

In a further aspect, the residues x and y are in the B domain. The first amino acid sequence may contribute at least about 80%, about 85%, about 90%, about 95%, or about 98% of the amino acid residues of the B domain.

Another aspect contemplates a hybrid amylase having an altered level of recombinant expression, solubility, pH activity profile, substrate specificity, or specific activity compared to the wild-type Termamyl-like alpha-amylase. The hybrid amylase may have alpha-amylase activity that is not affected by $Ca^{2+}$ concentration.

Also contemplated is a nucleic acid encoding the hybrid amylase as presently disclosed. A further aspect is a vector comprising the nucleic acid. A further aspect contemplates a host cell containing the nucleic acid or the vector. The host cell may be a bacterium or fungus. In yet another aspect, the bacterium may be *Bacillus* sp.

A further aspect contemplates a method of designing the nucleic acid than encodes the hybrid enzyme. The method comprises aligning a 3D structure of an archae alpha-amylase and a wild-type Termamyl-like alpha-amylase in a computer-implemented process, selecting the amino acid residues x and y that are structurally conserved, and designing the nucleic acid to encode the hybrid enzyme. The computer-implemented process may comprise displaying the 3D structural alignment on a computer monitor. The root mean square distance between alpha carbons in residues x and y compared to the wild-type Termamyl-like alpha-amylase 3D structure is no more than about 0.5 Å, about 0.4 Å, about 0.3 Å, about 0.2 Å, or about 0.1 Å.

BRIEF DESCRIPTION OF THE DRAWINGS

The accompanying drawings are incorporated in and constitute a part of this specification and illustrate various embodiments.

FIG. 1 depicts an amino acid sequence alignment and consensus sequence between a mature form (i.e., lacking a signal sequence) of *B. stearothermophilus* alpha-amylase ("MatAmyS": SEQ ID NO: 10) and a mature form of des-Met Ultrathin amylase ("MatUltrathin": SEQ ID NO: 9).

FIG. 2 depicts the relative activities of various amylases using the colorimetric Phadebas® amylase test (Magle Life Sciences). The substrate consists of water insoluble starch microspheres with chemically attached blue dye that is water soluble. Amylases hydrolyze the starch, releasing the blue dye that is measured by a change in adsorption at 620 nm A dilution series of culture supernatant sample were tested at both pH 7 (Panel A) and pH 10 (Panel B). Arbitrary units of absorbance are plotted as a function of dilution of the amylase test samples. The following hybrid amylases were analyzed:

Figure 5A:
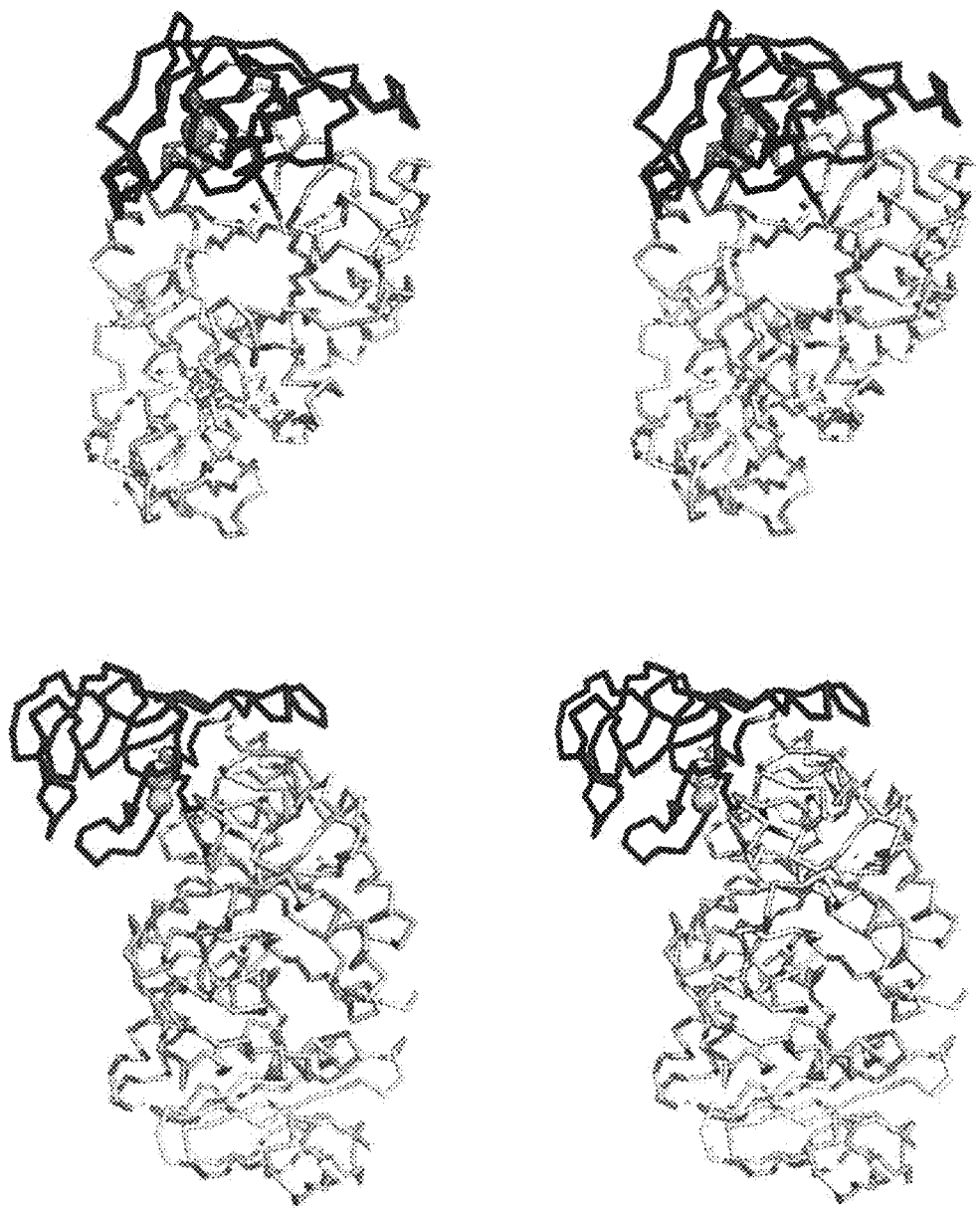

Hybrid A: UT 1-104: AmyS 100-483 (SEQ ID NO: 1);
Hybrid B: UT 1-113: AmyS 109-483 (SEQ ID NO: 2);
Hybrid C: UT 1-128: AmyS 140-483 (SEQ ID NO: 3);
Hybrid D: UT 1-145: AmyS 161-483 (SEQ ID NO: 4);
Hybrid E: UT 1-163: AmyS 203-483 (SEQ ID NO: 5);

Hybrid F: UT 1-175: AmyS 215-483 (SEQ ID NO: 6);
Hybrid G: UT 1-191: AmyS 228-483 (SEQ ID NO: 7); and
Hybrid H: UT 1-209: AmyS 246-483 (SEQ ID NO: 8).

FIG. 3 depicts the amino acid sequence of des-Met Ultrathin amylase (SEQ ID NO: 9). The bolded, underlined amino acid residues mark the various C-terminal residues of the Ultrathin portion in the hybrids shown in FIG. 2. The "cross-over positions" in Ultrathin are bolded and underlined.

FIG. 4 depicts the amino acid sequence of an AmyS variant having a C-terminal truncation that removes a starch binding domain (SEQ ID NO: 11). The bolded, underlined amino acid residues mark the N-terminal residues of the AmyS portion in the hybrids shown in FIG. 2. The "crossover positions" in AmyS are bolded and underlined.

FIG. 5A depicts two stereoscopic views of AmyS, with the B-domain in black. The spheres behind the B-domain represent atoms of bound $Na^+$ and $Ca^{2+}$.

FIG. 5B depicts two stereoscopic views of UT 1-104: AmyS 100-483, with residues UT 1-104 in black. The spheres behind the B-domain represent atoms of bound $Na^+$ and $Ca^{2+}$.

FIG. 5C depicts two stereoscopic views of UT 1-209: AmyS 246-483, with residues UT 1-209 in black. The spheres behind the B-domain represent atoms of bound $Na^+$ and $Ca^{2+}$.

DETAILED DESCRIPTION

Hybrid alpha-amylases are provided that share a conserved 3D structure in whole or in part with a wild-type Termamyl-like α-amylase, e.g., a *Bacillus* amylase. In the hybrid, an N-terminal portion of a Termamyl-like α-amylase is replaced with sequences from an archae α-amylase. The sequence similarity between the two amylases may be less than 60%. Conserving the wild-type 3D structure in the hybrid facilitates obtaining enzymatically active amylases. In one embodiment, one or both amylase sequences contribute residues to the B domain, resulting in particularly advantageous properties. For instance, replacement of the $Ca^{2+}$ binding site in the B domain of the Termamyl-like α-amylase with a B domain sequence of an archae α-amylase that does not bind $Ca^{2+}$ can produce a hybrid that is fully active in the absence of $Ca^{2+}$.

1. Definitions and Abbreviations

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1. Definitions

"Archae," as used herein, refers to single-cell organisms of a kingdom distinct from prokaryotes and eukaryotes. Archae include thermophiles, halophiles, and methanogens.

Amylases are hydrolases that cleave the α-D-(1→4) O-glycosidic linkages in starch and include glucoamylases and β-amylases, as well as alpha-amylases. For the purpose of this disclosure, however, "amylase" refers to an alpha-amylase unless otherwise designated. Alpha-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from starch.

A "Termamyl-like" amylase has at least about 60% sequence identity to wild-type *B. licheniformis* alpha-amylase.

A "wild-type" enzyme refers to an enzyme that occurs naturally. A "wild-type Termamyl-like α-amylase thus refers to a naturally occurring α-amylase has at least about 60% sequence identity to wild-type *B. licheniformis* alpha-amylase.

"Percent sequence identity" is determined by aligning two sequences and comparing them using the BLAST program with default alignment values, available at the website of the National Center for Biotechnology Information (NCBI) of the National Library of Medicine.

A "variant," or "variants" refers to either polypeptides or nucleic acids. For the purpose of the present disclosure, a "variant" includes hybrid proteins containing amino acid sequences from two different parent amylases. The term "variant" may be used interchangeably with the term "mutant." Variants include insertions, substitutions, transversions, truncations, and/or inversions at one or more locations in the amino acid or nucleotide sequence, respectively, compared to the wild-type sequence. The phrases "variant polypeptide," and "variant enzyme" thus mean a protein that has an amino acid sequence that has been modified from the amino acid sequence of a wild-type protein. The variant polypeptides include a polypeptide having a certain percent, e.g., at least about 80%, 85%, 90%, 95%, or 99%, of sequence identity with the parent enzyme. Variants may have 1, 2, 3, 4, 5, 10, 15, 20, or 30 amino acid substitutions, additions, or deletions, or any integral value within the range of 1-30, compared to the wild-type sequence. A variant may be expressed as a fusion protein containing a heterologous polypeptide. For example, the variant can comprise a signal peptide of another protein or a sequence designed to aid identification or purification of the expressed fusion protein, such as a His-Tag sequence.

The term "fusion protein" refers to two or more polypeptides joined together by any means known in the art. These means include chemical synthesis or splicing the encoding nucleic acids by recombinant engineering.

As used herein, the term "hybrid protein" is a special form of fusion protein. Like a fusion protein, an amino acid sequence from a first protein, an archae alpha-amylase, is fused or joined to an amino acid sequence from a second protein, a Termamyl-like alpha-amylase, to form a hybrid protein. In the hybrid alpha-amylase of the present disclosure, the first amino acid sequence from an archae alpha-amylase replaces a portion of a Termamyl-like alpha-amylase, while conserving all or part of the 3D structure of the replaced portion of the Termamyl-like alpha-amylase. The archae alpha-amylase and/or the Termamyl-like alpha-amylase, from which the hybrid amylase derives, may be "variants" of a wild-type amylase.

"Alpha carbon" refers to the backbone carbon in a polypeptide chain, the carbon that is bonded to the carbonyl carbon.

As used herein, a first 3D structure or fold or portion thereof is "structurally conserved" with a second 3D structure or portion thereof when the structures are aligned so that the root mean square distance (RMSD) of alpha carbons is no more than about 1 Å. See also, Orengo et al, *Protein Eng.* 6: 485-500 (1993).

As used herein, the term "fragment" refers to a polynucleotide or polypeptide sequence that is less than full length, and is a sequence that comprises two or more amino acid or nucleic acid residues, e.g., 5, 10, 15, 20, 30, or 50 residues.

As used herein, the term "expression" refers to the process by which a polypeptide is produced based on the nucleic acid sequence of a gene. The process includes both transcription and translation.

"Isolated" means that the sequence is at least substantially free from at least one other component that the sequence is naturally associated and found in nature, e.g., genomic sequences.

"Purified" means that the material is in a relatively pure state, e.g., at least about 90% pure, at least about 95% pure, or at least about 98% pure.

"Thermostable" means the enzyme retains activity after exposure to elevated temperatures. The thermostability of an enzyme is measured by its half-life ($t_{1/2}$), where half of the enzyme activity is lost by the half-life. The half-life value is calculated under defined conditions by measuring the residual amylase activity. To determine the half-life of the enzyme, the sample is heated to the test temperature for 1-10 min, and activity is measured using a standard assay for the activity of the enzyme.

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

"Homologue" means an entity having a certain degree of sequence identity with the subject amino acid sequences and the subject nucleotide sequences. A "homologous sequence" includes a polynucleotide or a polypeptide having a certain percent, e.g., at least about 80%, 85%, 90%, 95%, or 99%, of sequence identity with another sequence. Typically, homologues will comprise the same active site residues as the subject amino acid sequence. Homologues also retain enzymatic activity, although the homologue may have different enzymatic properties than the wild-type enzyme.

As used herein, "hybridization" includes the process by which a strand of nucleic acid joins with a complementary strand through base pairing, as well as the process of amplification as carried out in polymerase chain reaction (PCR) technologies. The variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The variant nucleic acid may be codon-optimized to further increase expression.

As used herein, a "synthetic" compound is produced by in vitro chemical or enzymatic synthesis. It includes, but is not limited to, variant nucleic acids made with optimal codon usage for host organisms, such as a yeast cell host or other expression hosts of choice.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, "biologically active" refers to a sequence having a similar structural, regulatory or biochemical function as the naturally occurring sequence, although not necessarily to the same degree.

As used herein the term "starch" refers to any material comprised of the complex polysaccharide carbohydrates of plants, such as corn, comprised of amylose and amylopectin with the formula $(C_6H_{10}O_5)_x$, where X can be any number.

1.2. Abbreviations

The following abbreviations apply unless indicated otherwise:

3-D or 3D three-dimensional
ADA azodicarbonamide
AmyS *B. stearothermophilus* (a/k/a *Geobacillus stearothermophilus*) amylase;
AmyS n Residue n of AmyS, using the numbering scheme of SEQ ID NO: 9
AmyS n-483 AmyS residues n-483, using the numbering scheme of SEQ ID NO: 9
cDNA complementary DNA
DEAE diethylamino ethanol
DNA deoxyribonucleic acid
EC Enzyme Classification designation
HPLC high performance liquid chromatography
mRNA messenger ribonucleic acid
PCR polymerase chain reaction
PDB protein database
PEG poly (ethyleneglycol)
ppm parts per million
RMSD root mean square distance
RT-PCR reverse transcriptase polymerase chain reaction
SDS-PAGE sodium dodecyl sulfate-polyacrylamide gel electrophoresis
1×SSC 0.15 M NaCl, 0.015 M sodium citrate, pH 7.0
$t_{1/2}$ half life
Tm melting temperature (° C.) at which 50% of the subject protein is melted
ΔTm ° C. change in Tm
Ultrathin archae amylase disclosed in GenBank™ Acc. No. AAM48115.1 (SEQ ID NO: 10)
UT n Residue n of Ultrathin amylase, using the numbering scheme of SEQ ID NO: 10
UT 1-n Ultrathin residues 1-n, using the numbering scheme of SEQ ID NO: 10
UT 1-x: Amy S y-483 Ultrathin residues 1-x fused to AmyS residues y-483
w/v weight/volume w/w weight/weight 2. Engineering Fusion Proteins with Conserved 3D Structure Domain structure may be disrupted when fusing dissimilar amino acid sequences to make a hybrid enzyme, particularly when the two sequences are joined in the middle of a domain. Disruption of domain structure in turn may lead to lower activity and/or difficulties in protein folding, resulting in a loss of yield of the expressed fusion protein. This problem is addressed by selecting an appropriate point of fusion between the amino acid sequence from the first protein and the amino acid sequence from the *Bacillus* protein. Namely, the two sequences are fused at a point where the 3D structure of the two amylase sequences is conserved. In this manner, minimal 3D structural alterations occur when the two sequences are joined in the hybrid enzyme. Further, this approach facilitates the construction of active hybrids, even when the amylases share less than 60% sequence identity.

A structural alignment of two proteins can be used to determine whether all or part of the 3D structure is conserved between two proteins. To this end, the 3D structure of a first protein can be superimposed onto or aligned with the 3D structure of a second protein. The superimposition or alignment can be made across the entire protein structure or elements of secondary structure. For example, secondary structure elements, such as the central β-strands in a β-barrel, can be aligned. Methods of superimposing or aligning structures are known in the art. In one embodiment, the aligning is conducted with a computer-implemented process, such as the Molecular Operating Environment alignment algorithm provided by Chemical Computing Group. In another embodiment, the output of the alignment is displayed on a computer monitor or display system.

Upon alignment of the two structures, the extent of alignment of the alpha carbon chains for the two structures can be determined. Amino acids that are structurally conserved are selected. For the purpose this disclosure, a first 3D structure or fold is "structurally conserved" with a second 3D structure when the RMSD of alpha carbons in the structures is no more than about 1 Å. The structural conservation may extend through at least two or more amino acid residues and may include the entire portion of the hybrid amylase contributed by the archae α-amylase. In one embodiment, the degree of structural conservation is sufficiently high so that the RMSD of alpha carbons is no more than about 0.5 Å.

The hybrid amylase has the general structure, from N-terminus to C-terminus, shown in formula (I):

A-x-y-B  (I), where A is a first amino acid sequence form an archae α-amylase, B is a second amino acid sequence from a wild-type Termamyl-like α-amylase or a variant thereof, x is the C-terminal residue of the first amino acid sequence, and y is the N-terminal residue of the second amino acid sequence. In one embodiment, at least residues x and y are structurally conserved with the wild-type Termamyl-like α-amylase. That is, the RMSD of alpha carbons in residues x and y is no more than about 1 Å. In another embodiment, the RMSD of alpha carbons in residues x and y is no more than about 0.5 Å.

Representative amino acid residues corresponding to x in formula (I) are shown as bolded, underlined amino acid residues depicted in FIG. 3. Representative amino acid residues corresponding to y in formula (I) are shown as bolded, underlined amino acid residues depicted in FIG. 4. Residues x and y occur at "cross-over positions."

The process of joining sequences of the two amylases to form the hybrid may be done by any method know in the art. For example, the amino acid sequences can be joined through a chemical conjugation of the amino acids at the termini of the polypeptide sequences. Alternatively, encoding nucleic acids can be recombinantly engineered to encode the hybrid protein in an expression host cell. Methods of recombinant engineering are well know in this art. Appropriate methods can be found, for example, in any currently available laboratory manual, such as Sambrook et al., MOLECULAR CLONING: A LABORATORY MANUAL, 3$^{rd}$ ed., Cold Spring Harbor Laboratory Press, Cold Spring Harbor, N.Y. (2001).

3. The Domain Structure of *Bacillus* Amylases

*Bacillus* alpha-amylase is made up of three globular domains A, B, and C. See WO 96/23874 for a full discussion. The domains can be defined as being residues 1-103 and 206-395 for domain A, residues 104-205 for domain B, and residues 396-483 for domain C, the numbers referring to *B. licheniformis* alpha-amylase. *Bacillus* alpha-amylase is an elongated molecule, the longest axis being about 85 Å. The widest point perpendicular to this axis is approximately 50 Å and spans the central A domain. The active site residues of the *B. licheniformis* alpha-amylase are D323, D231 and E261.

3.1. Domain A

Domain A is the largest domain and contains the active site, comprised of a cluster of three amino acid residues in a deep cleft in the enzyme's surface. Domain A of all known alpha-amylase structures has the same overall fold, namely, the (β/α)$_8$ barrel with eight central β-strands and eight flanking α-helices. The C-terminal end of β-strand 1 is connected to helix 1 by a loop denoted loop 1, and an identical pattern is found for the other loops. These loops show some variation in size and some can be quite extensive.

The eight central β-strands in the (β/α)$_8$ barrel superimpose well between the various known α-amylase structures, and this part of the structure, including the close surroundings of the active site located at the C-terminal end of the β-strands, show high similarity between the different amylases.

The loops connecting β-strands and α-helices display high variations between Termamyl-like alpha amylases and fungal alpha-amylases. These loops constitute the structural context of the active site and the majority of the contacts to the substrate is found among residues located in these loops. Such important characteristics as substrate specificity, substrate binding, pH/activity profile, starch cleavage pattern are determined by the amino acids and the positions of same in these loops.

3.2. Domain B

Domain B is a compact domain having a very high number of charged residues. The B domain arises as an extension of the loop between strand 3 and helix 3 of domain A and contains a five-stranded antiparallel β-sheet structure containing at least one long loop structure and having the connectivity −1, +3, −1X, +2. See Richardson, *Adv. Protein Chem.* 34, 167-339 (1981).

The first four strands of the B domain form two hairpin loops, which twist around each other like a pair of crossed fingers (right-hand twist). The main chain folds into a β-strand, which connects two small β-sheet structures. After making one turn in one sheet, it folds back and makes up a two-stranded sheet in contact with domain A and an internal hole in the α-amylase structure. Then the main chain folds up to a small sheet structure nearly perpendicular to the first two sheets. Before entering the helix 3 on top of β-strand 3, the approximately 24 last amino acids in domain B form two calcium binding sites in the contact region to domain A.

Domain B is connected with domain A by two peptide stretches, which divide the domain-domain contact areas into two. Domain B is in contact with Domain A by a calcium binding region and an internally buried hole containing water molecules. Many types of molecular contacts are present. Ionic interacting between acid and basic amino acids are possible, these interactions are very important for the general stability at high pH and for keeping the calcium binding sites intact.

3.3. Domain C

Domain C is the C-terminal part of the protein consisting of amino acids 394-483. Domain C is composed entirely of β-strands, which form a single 8-stranded sheet structure that folds back on itself. The sheet structure thus may be described as a β-sandwich structure. The connectivity is +1, +1, +5, −3, +1, +1, −3, although strands 6 and 7 are only loosely connected. One part of the β-sheet forms the interface to domain A.

3.4. $Ca^{2+}$-Binding and $Na^+$-Binding Sites

The structure of the Termamyl-like α-amylase contains four calcium-binding sites and one sodium-binding site, although one of the calcium ions displays very weak coordination. Two of the calcium ions form part of a linear cluster of three ions, the central ion being attributed to sodium, which lies at the junction of the A and B domains.

For the calcium ion nearest to the active site, the backbone carbonyls from His235 and Asp194, a side chain atom from residues Asp194, Asn102 and Asp200, and one water molecule bind the calcium. For the sodium ion, the binding site involves Asp194, Asp200, Asp183 and Asp159, and a backbone carbonyl from Val201. The calcium binding site between domain A and B involves Asp204 and Asp159, backbone carbonyl from Asp183 and Ala181, an atom from Asp202, and one water molecule.

One calcium ion is located between the A and C domain, another is located in the C domain. The first mentioned calcium binds a carbonyl backbone from Gly300, Tyr302 and His406, atoms from Asp430, an atom from Asp407, and one water molecule. The weakly coordinated calcium site comprises four water molecules, and atoms from Glu447 and Asn444.

4. Hybrid Amylases

A hybrid amylase is provided that may be isolated and/or purified. The hybrid amylase comprises an N-terminal fragment of a first alpha-amylase and a C-terminal fragment of a second alpha-amylase, which is a *Bacillus* alpha-amylase. In one embodiment, the *Bacillus* alpha-amylase is a Termamyl-like amylase. In a specific embodiment, the *Bacillus* alpha-amylase is AmyS. The first and second amylases may share less than about 60% sequence identity in one embodiment. For example, the amylases may share less than about 50%, 40%, 30%, or 20% sequence identity. The first alpha-amylase sequences comprise at least about 10%, but no more than 80%, of the amino acid sequences of the hybrid. In various embodiments, the first alpha-amylase comprises at least about 10%, 20%, 30%, 40%, 50%, 60%, 70%, 80%, or any integral value between 10-80% of the amino acid residues of the hybrid.

The first alpha-amylase sequence, when used in the hybrid amylase, maintains a conserved 3D structure with part or all of the corresponding portion of the *Bacillus* alpha-amylase that is replaced in the hybrid. The first alpha-amylase may be an archae alpha-amylase. Archae alpha-amylases include Ultrathin, disclosed in GenBank™ Accession Number AAM48115.1 (SEQ ID NO: 11). Archae alpha-amylases, like Ultrathin, have a $Zn^{2+}$ binding site in the same general location of the B domain as the $Ca^{2+}$—$Na^+$—$Ca^{2+}$ binding site in *Bacillus* amylases. $Ca^{2+}$ has no significant effect on the stability or activity of archae alpha-amylases. Ultrathin shows a relatively weak sequence identity with AmyS, as depicted in FIG. 1. Ultrathin, however, displays relatively high similarity to AmyS at the level of 3D structure.

FIG. 5 shows stereoscopic depictions of the 3D structures of representative hybrid amylases. The structures are generated by a series of modeling algorithms described below in the Examples. In FIG. 5A, the B domain is shown in black. In FIG. 5B, N-terminal residues of AmyS are replaced by residues 1-104 of Ultrathin. Only a small fraction of the B domain is replaced in this embodiment. Comparison of the 3D structure of the hybrid in FIG. 5B with the wild-type AmyS structure in FIG. 5A demonstrates the high proportion of 3D structure that is conserved in the hybrid. The hybrid structure depicted in FIG. 5C depicts a hybrid in which N-terminal AmyS residues are replaced with residues 1-209 of Ultrathin. While the overall structure of the hybrid is similar to the *Bacillus* enzyme, not all the hybrid structure is necessarily "conserved," as the term is defined above.

In one embodiment, a hybrid amylase comprises the $Zn^{2+}$ binding region of the archae alpha-amylase, such as the Ultrathin alpha-amylase. The hybrid amylase thus may be made insensitive to the concentration of $Ca^{2+}$, while the hybrid retains the activity and structural stability characteristics of wild-type *Bacillus* alpha-amylase. For example, a hybrid amylase includes an AmyS C-terminal portion fused to a portion of Ultrathin containing the $Zn^{2+}$ binding site. Specific hybrids constructed along these lines contain various portions of the B domain of the Ultrathin (UT) alpha-amylase:

Hybrid A: UT 1-104: AmyS 100-483 (SEQ ID NO: 1);
Hybrid B: UT 1-113: AmyS 109-483 (SEQ ID NO: 2);
Hybrid C: UT 1-128: AmyS 140-483 (SEQ ID NO: 3);
Hybrid D: UT 1-145: AmyS 161-483 (SEQ ID NO: 4);
Hybrid E: UT 1-163: AmyS 203-483 (SEQ ID NO: 5);
Hybrid F: UT 1-175: AmyS 215-483 (SEQ ID NO: 6);
Hybrid G: UT 1-191: AmyS 228-483 (SEQ ID NO: 7); and
Hybrid H: UT 1-209: AmyS 246-483 (SEQ ID NO: 8).

Hybrid amylases may be engineered to provide amylases with improved properties, such as an altered requirement for $Ca^{2+}$, increased thermostability, altered specific activity, altered endo- or exo-amylase activity, or an altered pH optimum.

Nucleic acids encoding the hybrid amylases also are provided. By way of a non-limiting example, a nucleic acid encoding a hybrid amylase may be a cDNA encoding the protein of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. As is well understood by one skilled in the art, the genetic code is degenerate, meaning that multiple codons in some cases may encode the same amino acid. Nucleic acids include genomic DNA, mRNA, and cDNA that encodes a hybrid amylase. Representative nucleic acids encoding hybrid amylases include SEQ ID NOS: 20-27, which encode the hybrid amylases of SEQ ID NOS: 1-8, respectively.

4.1. Hybrid Amylases Having Variant Sequences

In an embodiment, a sequence comprising a hybrid amylase is a variant of the native or wild-type sequence. In an aspect, only the fragment of the hybrid corresponding to the first amylase is a variant with respect to its native sequence over the same contiguous residues. In another aspect, only the fragment of the hybrid corresponding to the *Bacillus* amylase is a variant with respect to its native sequence over the same contiguous residues. For example, the AmyS sequence may be selected from the AmyS having a C-terminal truncation set forth in SEQ ID NO: 11, which truncation removes a starch binding domain. In some embodiments, a host cell is genetically engineered to express a fold segment fusion variant with an amino acid sequence having at least about 80%, 85%, 90%, 95%, 96%, 97%, 98% or 99% identity with the SEQ ID NOS: 1-8.

Methods of genetic modification and recombinant production of amylases and variants thereof are well-known in the art and include those described in U.S. Pat. Nos. 7,166, 453; 6,890,572; and 6,667,065. Preparation of encoding polynucleotide sequences, primers, vectors, selection methods, host cells, purification and reconstitution of expressed amylase variants, and characterization of thereof, including useful buffers, pH ranges, substrate concentrations and enzyme concentrations for enzymatic assays, all are well-known in the art. Hybrid amylases comprised of variant sequences, as described herein, can also be produced synthetically or through recombinant expression in a host cell, according to procedures well known in the art.

5.0 Production of Fold Segment Fusions 5.1. Vectors

In some embodiments, a DNA construct comprising a nucleic acid encoding a hybrid amylase, including a variant of a hybrid amylase such as described above, is transferred to a host cell in an expression vector that comprises regulatory sequences operably linked to a hybrid amylase encoding sequence. The vector may be any vector that can be integrated into a host cell genome and replicated when introduced into the host cell. Additional examples of suitable expression and/or integration vectors are provided in Sambrook et al., MOLECULAR CLONING: A LABORATORY MANUAL, 3$^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Exemplary vectors include pFB6, pBR322, PUC18, pUC100 and pENTR/D, pDON™201, pDONR™221, pENTR™, pGEM®3Z and pGEM®4Z. Exemplary for use in bacterial cells include pBR322 and pUC19, which permit replication in *E. coli*, and pE194, for example, which permits replication in *Bacillus*.

In some embodiments, a nucleic acid encoding a hybrid amylase is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when a *Bacillus* cell is the expression host cell, the promoter is a native *Bacillus* promoter. An "inducible promoter" is a promoter that is active under environmental or developmental regulation. In another embodiment, the promoter is one that is heterologous to the host cell.

In some embodiments, the coding sequence is operably linked to a signal sequence. The DNA encoding the signal sequence may be the DNA sequence naturally associated with the hybrid amylase nucleic acid to be expressed. In other embodiments, the DNA encoding the signal sequence is replaced with a nucleotide sequence encoding a signal sequence from a species other than *Bacillus*. In this embodiment, the polynucleotide that encodes the signal sequence is immediately upstream and in-frame of the polynucleotide that encodes the polypeptide. The signal sequence may be selected from the same species as the host cell. In one non-limiting example, the signal sequence is a cyclodextrin glucanotransferase (CGTase; EC 2.4.1.19) signal sequence from *Bacillus* sp., and the hybrid amylase is expressed in a *B. subtilis* host cell. A methionine residue may be added to the N-terminus of the signal sequence.

In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source. The use of an *A. nidulans* amdS gene as a selective marker is described in Kelley et al., (1985) *EMBO J.* 4: 475-479 and Penttila et al., (1987) *Gene* 61: 155-164.

A suitable expression vector comprising a DNA construct with a polynucleotide encoding a hybrid amylase may be any vector that is capable of replicating autonomously in a given host organism or integrating into the DNA of the host. In some embodiments, the expression vector is a plasmid. In some embodiments, two types of expression vectors for obtaining expression of cDNA are contemplated. The first expression vector comprises DNA sequences in which the promoter, hybrid amylase coding region, and terminator all originate from the cDNA sequence to be expressed. In some embodiments, gene truncation is obtained by deleting undesired DNA sequences, e.g., DNA encoding the C-terminal starch binding domain, to leave the domain to be expressed under control of its own transcriptional and translational regulatory sequences. The second type of expression vector is preassembled and contains sequences required for high-level transcription and a selectable marker. In some embodiments, the coding region for a hybrid amylase cDNA or part thereof is inserted into this general-purpose expression vector, such that it is under the transcriptional control of the expression construct promoter and terminator sequences. In some embodiments, genes or part thereof are inserted downstream of the strong cbh1 promoter.

5.2. Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., (1989) *Curr. Genet.* 16: 53-56. The expression of heterologous protein in *Trichoderma* is described, for example, in U.S. Pat. No. 6,022,725; U.S. Pat. No. 6,268,328; Harkki et al., (1991) *Enzyme Microb. Technol.* 13: 227-233; Harkki et al., (1989) *BioTechnol.* 7: 596-603; EP 244,234; and EP 215,594. In one embodiment, genetically stable transformants are constructed with vector systems whereby the nucleic acid encoding a hybrid amylase is stably integrated into a host cell chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

Exemplary host cells include a Gram positive bacterium such as *Bacillus subtilis*, *B. licheniformis*, *B. lentos*, *B. brevis*, *B. stearothermophilus*, *B. alkalophilus*, *B. amyloliquefaciens*, *B. coagulans*, *B. circulans*, *B. lautus*, *B. thuringiensis*, *Streptomyces lividans*, or *S. murinus*; or a Gram negative bacterium, wherein such as *Escherichia coli* or a *Pseudomonas* species.

6.0 Production and Characterization of Hybrid Amylases
6.1. Methods for purifying hybrid amylases In general, a hybrid amylase produced in cell culture is secreted into the medium and may be purified or isolated, e.g., by removing unwanted components from the cell culture medium. In some cases, a hybrid amylase may be recovered from a cell lysate. In such cases, the hybrid amylase is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAE, chromatofocusing, SDS-PAGE, ammonium sulfate precipitation, and gel filtration using Sephadex G-75, for example. Other techniques for protein purification are well-known in the art and widely available.

6.2. Identification of hybrid amylase activity

To evaluate the expression of a hybrid amylase in a host cell, assays can be used to measure the expressed protein, corresponding mRNA, or α-amylase activity. Exemplary assays include Northern and Southern blotting, RT-PCR (reverse transcriptase polymerase chain reaction), and in situ hybridization, using an appropriately labeled hybridizing probe. Assays also include measuring hybrid amylase activity in a sample. Assays for exo-activity of a expressed hybrid amylase include, but are not limited to, the Betamyl® assay (Megazyme, Ireland). Suitable assays of the endo-activity of a hybrid amylase include, but are not limited to, the Phadebas® amylase test (Magle Life Sciences). Assays also include HPLC analysis of liquefact prepared in the presence of a hybrid amylase. HPLC can be used to measure amylase activity by separating DP-3 and DP-4 saccharides from other components of the assay.

6.3. Hybrid Amylase Variant Characterization

Hybrid amylases can be characterized by their nucleic acid and primary polypeptide sequences, by three dimensional structural modeling, and/or by their specific activity. Additional characteristics of the hybrid amylase include stability, pH range, oxidation stability, and thermostability, for example. Levels of expression and enzyme activity can be assessed using standard assays known to the artisan skilled in this field. In another aspect, variants demonstrate improved performance characteristics relative to the wild-type enzyme, such as improved stability at high temperatures, e.g., 65-85° C. Hybrid amylases are advantageous for use in liquefaction or other processes that require elevated temperatures, such as baking. For example, a thermostable hybrid amylase can degrade starch at temperatures of about 55° C. to about 85° C. or more.

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant enzyme.

A nucleic acid complementary to a nucleic acid encoding any of the hybrid amylases set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast.

7. Compositions and Uses of Hybrid Amylases

A hybrid amylase produced and purified by the methods described herein is useful for a variety of industrial applications. The desirability of using a particular hybrid amylase will depend on the overall properties displayed by the hybrid amylase relative to the requirements of a particular application.

In one embodiment, the hybrid amylase is useful in a starch conversion process, particularly in a liquefaction process of a starch, e.g., cornstarch, wheat starch, or barley starch. The desired end-product may be any product that may be produced by the enzymatic conversion of the starch substrate. For example, the desired product may be a syrup rich in saccharides useful for fermentation, particularly maltotriose, glucose, and/or maltose.

*Bacillus* amylases are commonly used to catalyze the degradation of a starch suspension, which may contain 30-40% w/w dry solids (ds), to maltodextrans. Because liquefaction typically is conducted at high temperatures, e.g., 90-100° C., thermostable α-amylases, such as *Bacillus* amylases, are preferred for this step. *Bacillus* amylases typically do not produce significant amounts of glucose. Instead, the resulting liquefact has a low dextrose equivalent (DE) and contains maltose and sugars with high degrees of polymerization (DPn).

The liquefact thus is usually subjected to an additional saccharification reaction, which may be catalyzed by glucoamylases and/or maltogenic α-amylases. These enzymes catalyze the hydrolysis of non-reducing ends of the maltodextrans formed after liquefaction, releasing D-glucose, maltose and isomaltose. Saccharification produces either glucose-rich or high-maltose syrups. In the former case, glucoamylases typically catalyze saccharification under acidic conditions at elevated temperatures, e.g., 60° C., pH 4.3. Glucoamylases used in this process typically are obtained from fungi, e.g., *Aspergillus niger* glucoamylase used in Optidex® L400 or *Humincola grisea* glucoamylase. De-branching enzymes, such as pullulanases, can aid saccharification. Glucoamylases, however, typically do not perform well in the presence of $Ca^{2+}$. For this reason, $Ca^{2+}$ used to support optimal activity of the *Bacillus* amylases in the liquefaction step must be removed prior to saccharification in a time consuming operation.

The hybrid amylases disclosed herein are particularly advantageous when used in a process of liquefying starch. Because the some of the present hybrid amylases do not require $Ca^{2+}$ for activity, they can be used to liquefy starch in the absence of added $Ca^{2+}$. The liquefied starch then can be saccharified directly with a glucoamylase, without the requirement of first removing $Ca^{2+}$, speeding the overall reaction and increasing the efficiency of sugar production.

It will be apparent to those skilled in the art that various modifications and variation can be made to the compositions and methods of using same without departing from the spirit or scope of the intended use. Thus, it is the modifications and variations provided they come within the scope of the appended claims and their equivalents.

EXAMPLES

Example 1

1.1. Alignment of Amylase Structures

In a preliminary step, the 3D structure of *Pyrococcus woesei* amylase (PDP Accession No. 1MXG) was aligned with a 3D structure of AmyS (PDB Accession No. 1HVX). The archae alpha-amylase des-Met Ultrathin (GenBank™ Accession No. AAM48115.1; SEQ ID NO: 9) 3D structure then was determined using the *Pyrococcus woesei* structure as a guide. Ultrathin shares a high level of sequence identity (86.7%) to the *Pyrococcus woesei* amylase, facilitating the construction of an accurate 3D structural model. Modeling was performed with the ClustalW program. See Thompson et al., *Nucleic Acids Res.* 22: 4673-46 (1994).

Finally, the des-Met Ultrathin structure was aligned with AmyS using ClustalW. Final superposition was based on aligned alpha carbons with a RMSD from each other of about 1 Å. Aligned residues having alpha carbons having a RMSD of 0.5 Å were identified as preferred positions to join the Ultrathin and AmyS sequences in the hybrid amylase.

1.2. Hybrid Construction and Expression

Nucleic acids encoding hybrid amylases were designed and constructed. For the purpose of this example, the hybrid amylases of SEQ ID NOS: 1-8 have the abbreviations shown in TABLE 2. The parentheses before and after the residue numbers indicate amino acid residues that are connected in the fusion protein. The position of these residues with respect to the full length sequence of Ultrathin and AmyS are depicted in FIGS. 3 and 4, respectively. The Ultrathin residues in parentheses represent residue x in formula (I), A-x-y-B, whereas AmyS residues in the parentheses represent residue y in formula (I).

TABLE 2

| Fusion protein | Ultrathin residues | AmyS residues |
| --- | --- | --- |
| A (SEQ ID NO: 1) | 1-104 (I) | (A) 100-483 |
| B (SEQ ID NO: 2) | 1-113 (A) | (G) 109-483 |
| C (SEQ ID NO: 3) | 1-128 (W) | (T) 140-483 |
| D (SEQ ID NO: 4) | 1-145 (D) | (F) 161-483 |
| E (SEQ ID NO: 5) | 1-163 (P) | (D) 203-483 |
| F (SEQ ID NO: 6) | 1-175 (W) | (L) 215-483 |
| G (SEQ ID NO: 7) | 1-191 (G) | (I) 228-483 |
| H (SEQ ID NO: 8) | 1-209 (K) | (D) 246-483 |

Hybrid A was synthesized chemically using standard techniques well known in the art. Hybrid A was used as a backbone to clone in the remaining hybrids. The hybrid A encoding nucleic acid is 1551 base pairs in length and contains a BssHII restriction site at position 1199. The remaining hybrid genes were synthesized up to the BssHII restriction site, since they all contain the same sequence of DNA from this restriction site to the end of the gene. This allowed for ease of cloning into a vector containing the hybrid A backbone up to BssHII site.

A plasmid was constructed having the following elements: a beta lactamase gene, which confers ampicillin/carbenicillin resistance; a *B. subtilis* AprE (alkaline protease) promoter, which has a region of homology to the *Bacillus* host chromosome that promotes integration into the host genome; a *B. subtilis* AprE signal sequence; the hybrid amylase encoding nucleic acid; a *B. licheniformis* LAT (*licheniformis* amylase thermostable) terminator; a chloramphenicol acetyl transferase gene for chloramphenicol resistance; and an *E. coli* origin of replication.

The nucleic acids encoding hybrid amylases were amplified using PCR with the following primers:

```
PstI-NheI-F:
                               (SEQ ID NO: 12)
ctcagctctgcagctagcgcagcaa BssHII-Ethyl Rev:
                               (SEQ ID NO: 13)
gtgtggaattgtgagcggcca
```

The PCR reaction contents included 5 µL pFU UltraBuffer (10×), 42 µL H₂O, 0.5 µL Primer: PstI-NheI-F, 0.5 µL Primer: BssHII-Ethyl Rev, 1 µL Roche dNTP's (5 mM stock solution). 1 µL hybrid DNA and 1 µL pFU Ultra HF DNA Polymerase. The PCR Program cycle was 1 minute at 95° C., 18× (1 minute 95° C., 1 minute 60° C., 2 minutes, 20 seconds at 68° C.), followed by 7 minutes at 68° C. and a hold at 4° C., using a thermal cycler (MJ Research® PTC-200 Peltier).

The amplified linear 1.5 Kb fragment was purified using a Qiagen® Qiaquick PCR purification kit. Plasmid pJH101, an integrating vector for expression in *Bacillus subtilis* (Ferrari et al., *J. Bacteriol.* 154: 1513-15 (1983)) was used for the expression of all the hybrid amylases. The hybrid A gene and the integrating vector (pJH101) were both double-digested with restriction enzymes HindIII and NheI in order to generate cohesive sticky ends, and the hybrid A gene was ligated into vector pJH101 using a T4 DNA ligase DNA ligation kit (Takara Bio, catalog number 6023 kit). One hundred µL of Top 10 competent *E. coli* cells (Invitrogen) were transformed with 5 µL ligation reaction and plated onto LA (Luria Agar) +50 ppm carbenicillin and incubated at 37° C. overnight. After the bacterial colonies had grown, individual clones were selected to perform Colony PCR using puReTaq Ready-To-Go PCR Beads™ from GE Healthcare. Colonies were picked and transferred directly into the PCR tubes. The PCR primers used were:

```
pAprBbsGTG-201-fwd:
                               (SEQ ID NO: 14)
agcgagagatgatataccta pJH101-end-rev:
                               (SEQ ID NO: 15)
tttcggcgtgggtatggtggc
```

DNA from each PCR reaction was separated on agarose gels to confirm that the Colony PCR had been successful.

Clones were then sent to QuintaraBio (Berkeley, Calif.) for DNA sequencing analysis using the following primers:

```
pAprBbsGTG-201-fwd:
                                         (SEQ ID NO: 14)
    agcgagagatgatataccta pJH101-end-rev:
                                         (SEQ ID NO: 15)
    tttcggcgtgggtatggtggc Et538-fwd:
                                         (SEQ ID NO: 16)
    ggtggacgccgtcgaagtcaat Et1130-F:
                                         (SEQ ID NO: 17)
    cgcacgttaatgaccaatacac
```

The remaining hybrids were cloned using the hybrid A vector. The genes for hybrids B, C, E, F, G, and H were cut directly out of the vector supplied by Gene Oracle Inc. Briefly, E. coli stabs supplied by Gene Oracle Inc. were streaked onto LA+50 ppm carbenicillin plates and cultures were grown overnight at 37° C. DNA from these cultures was prepared using the Qiagen Miniprep Kit.

The genes for hybrids B, C, E, F, G, and H were double-digested with restriction enzymes BssHII and NheI in order to generate cohesive sticky ends. These sticky ends allowed for direct ligation of the hybrid genes into the backbone vector of hybrid A. The hybrid genes were gel-extracted and purified using Qiagen Gel Extraction Kit. The hybrid genes were ligated into the backbone vector of hybrid A using a T4 DNA ligase DNA ligation kit (Takara Bio, catalog number 6023 kit).

The gene for hybrid D was amplified using the following primers:

```
PstI-NheI-F:
                                         (SEQ ID NO: 18)
    ctcagctctgcagctagcgcagcaa BssHII-Eth-new2R:
                                         (SEQ ID NO: 19)
    gacgacgagcgcgcgatcagaag
```

The PCR reaction contents included 5 µL pFU UltraBuffer (10×), 42 µL H₂O, 0.5 µL Primer: PstI-NheI-F, 0.5 µL Primer: BssHII-Eth-new2R, 1 µL Roche dNTP's (5 mM stock solution), 1 µL Ultra-Ethyl Hybrid DNA and 1 µL pFU Ultra HF DNA Polymerase. The PCR Program cycle was 2 minute 95° C., 18× (1 minute 95° C., 1 minute 56° C., 1 minute, 15 seconds, at 68° C.), 1 minute, 15 seconds at 68° C. followed by a hold at 4° C. using a MJ Research® PTC-200 Peltier thermal cycler.

Generally, after performing PCR of a particular gene, only about 2-5 µL per reaction is analyzed on agarose gel to confirm that the DNA amplified correctly. The rest of the original reaction was purified using a Qiagen PCR Purification Kit. However, in this instance, two bands were observed on the analytical gel. Therefore, the entire PCR reaction was applied to an agarose gel to extract and purify the band that corresponded to the correct DNA length (~1100 base pairs). DNA was isolated from the gel using a Qiagen Gel Extraction Kit.

Subsequently, the purified linear fragment (~1100 base pairs) was digested sequentially using BssHII and NheI enzymes. The entire sample was purified using Qiagen PCR Purification Kit. The backbone vector of hybrid A was also digested similarly and was gel extracted using the Qiagen Gel Extraction Kit. The hybrid D gene was ligated into the backbone vector of hybrid A using Takara Bio—lot #6023 kit. Top 10 competent E. coli cells (Invitrogen) were transformed with 5 µL of each ligation reaction and transformation reactions were plated onto LA+50 ppm carbenicillin and incubated at 37° C. overnight.

The ligation reactions for hybrids B, C, E, F, G, and H were amplified using a Rolling Circle Amplification (RCA) TempliPhi kit (Amersham cat. #25 6400) as per the manufacturer's protocol. Top 10 competent E. coli cells (Invitrogen) were transformed with 5 µL of each ligation reaction and transformation reactions were plated onto LA+50 ppm carbenicillin and incubated at 37° C. overnight.

Single clones were selected from cultures of all hybrid constructs. Colony PCR was performed on single colonies using puReTaq Ready-To-Go PCR Beads (GE Healthcare). Colonies were directly picked into the PCR tubes. The PCR primers used were:

```
pAprBbsGTG-201-fwd:
                                         (SEQ ID NO: 14)
    agcgagagatgatataccta pJH101-end-rev:
                                         (SEQ ID NO: 15)
    tttcggcgtgggtatggtggc
```

An agarose gel was run to confirm that the Colony PCR reaction had been successful. Clones were then sent to QuintaraBio for sequencing analysis using the following primers:

```
pAprBbsGTG-201-fwd:
                                         (SEQ ID NO: 14)
    agcgagagatgatataccta pJH101-end-rev:
                                         (SEQ ID NO: 15)
    tttcggcgtgggtatggtggc Et538-fwd:
                                         (SEQ ID NO: 16)
    ggtggacgccgtcgaagtcaat Et1130-F:
                                         (SEQ ID NO: 17)
    cgcacgttaatgaccaatacac
```

Liquid cultures of clones with correct DNA sequences were frozen in 15% total volume glycerol at −80° C.

Plasmid minipreps were performed on clones using Qiagen Miniprep kit. Samples of 5 µL plasmid DNA (0.4-0.5 µg) were transformed into 100 µL BG6006 Bacillus cells (phenotype: DaprE, DnprE, Depr, DispA, Dbpr, Dvpr, DwprA, Dmpr-ybfJ, DnprB, degUHy32, oppA, DspoIIE3501, amyE::xylRPxylAcomK-ermC). The reaction mixtures were incubated in a shaker at 37° C. for 1 hour and plated onto 1% Insoluble Corn starch, +5 ppm Chloramphenicol and incubated at 37° C., overnight (at least 16 hours). Plasmid pJH101 is an integrating vector (lacking an origin of replication for Bacillus) and therefore has the ability to integrate itself into the host's genome. Plasmid integration was accomplished by plating the cells onto higher concentrations of antibiotic, which forced the vector to insert multiple copies of itself into the genome to survive in a high concentration of antibiotic. Specifically, colonies were re-streaked onto 1% insoluble starch +25 ppm chloramphenicol LB plates several times. In this instance, hybrids were re-streaked a total of 4 times before the colonies appeared to withstand the higher concentration of antibiotic. At this stage, the hybrids were ready to be assayed for amylase activity using the starch plate assay described below which relies on the change in turbidity of the starch within the plate matrix as a read-out for starch hydrolysis.

Example 2

2.1. Preparation Of Hybrid Amylases

Fresh glycerol stocks of the different hybrid amylases cloned in *B. subtilis* BG6006 host cells were streaked onto LB plates containing 1% insoluble corn starch+25 ppm chloramphenicol and incubated at 37° C. overnight. The next morning, starter cultures were grown in 5 mL of 25 ppm chloramphenicol-containing media. The starter culture was allowed to grow for 8 hours and 15 minutes in a shaker (250 rpm) at 37° C. Then, 30 µL of this pre-culture was added into a 250 mL flask filled with 30 mL of cultivation media (described below) supplemented with 25 ppm chloramphenicol and 5 mM $CaCl_2$. The shake flasks were incubated for 60-65 hours at 37° C., with mixing at 250 rpm. The cultivation media was an enriched semi-defined media based on MOPS buffer, with urea as major nitrogen source and glucose as the main carbon source, and supplemented with 1% soytone for robust cell growth. Following cell growth, the cultures were split into two sets: Set 1 was kept at a native pH of 7 and the pH of Set 2 cultures was increased to about 10.5. Twenty-five mL of cell suspension from each Set 1 culture was centrifuged at 5000 rpm for 20 minutes to separate the protein in the supernatant from the cell pellet. For Set 2, 1.5 mL of each culture was aliquoted into 2 ml centrifuge tubes and 1-3 µl of NaOH was added to increase pH to 10.5. The samples were centrifuged at 14,000 rpm for 5 minutes. The supernatants (containing proteins of interest) were transferred to clean tubes and placed in the refrigerator until ready to assay.

2.2. Phadebas Assay for Amylase Activity

The hybrid amylases prepared above were tested for amylase activity using the colorimetric Phadebas assay, where Ultrathin was used as a control. The results of the assay are depicted in FIG. 2. Culture supernatants from shake flasks of the different amylase hybrids (prepared as described above) were tested for amylase activity in Millipore multiscreen-HV plates (#MAHVN4550) using Phadebas® dye-linked starch substrate. Phadebas® amylase assay tablets from Magle Life Sciences were dissolved in assay buffer (50 mm Na maleate, 50 mM NaCl, 2 mM $CaCl_2$, pH 5.2) with occasional vortex mixing for 5-10 minutes. Fifteen µL of culture supernatant from each set of protein samples was added to 135 µL assay buffer on the top row of a 96 well plate (1:10 dilution) and samples were mixed by pipetting. A 50 µL aliquot from each of these wells was transferred to the row below, containing 100 µL assay buffer (1:3 dilution), mixed by pipetting, followed by serial transfer of 50 µL down the plate for subsequent dilutions. A 100 µL aliquot of substrate solution was added to each well. The plates were covered, mixed briefly on plate rotator/mixer and placed in an incubator at 37° C. for 45 minutes. Following this incubation, the plates were placed in a Millipore vacuum manifold, the contents were filtered into a standard flat-bottom plate, and the optical density measured at 620 nm in a microplate reader.

2.3. Starch Plate Assay for Amylase Activity

In this assay, the amylase production by cells expressing the different amylase hybrids was tested by plating the *Bacillus* clones on LA plates supplemented with 1% insoluble starch+25 ppm chloramphenicol and incubating the plates overnight (at least 16 h) at 37° C. The following day, the clones were ranked qualitatively by observing the presence of clearing zones on the starch plates and assigning a relative halo size. Ultrathin was used as a control. Although Ultrathin is typically cultured at 37° C., the assay plates had to be cultured at 70° C. to see halos.

2.4. Results

The results of the assays set forth in Examples 2.2. and 2.3. are depicted in FIG. 2 and TABLE 3, using Ultrathin as a control. The results of the halo assay are shown in the second column of TABLE 3, and the results of the colorimetric assay are shown in the third column

TABLE 3

| Hybrid | Halo Size | Relative enzyme activity |
|---|---|---|
| Ultrathin | Medium | 1.0 |
| A | Medium | 1.3 |
| B | Large | 0.3 |
| C | None | ND |
| E | None | ND |
| F | Small | 0.2 |
| G | Small | ND |
| H | Very large | 3.5 |

Hybrid B contains AmyS residues 109-483, meaning that it does not possess the B domain residue 102 that is involved in calcium binding. Nevertheless, this hybrid displays significant amylase activity, demonstrating the feasibility of forming hybrids from amylase sequences that each contain a portion of the B domain. Amylase activity measurements (as shown on both panels A and B of FIG. 2) suggest that hybrids, such as Hybrid A and Hybrid H, can hydrolyze insoluble starch much more effectively than the Ultrathin wild-type enzyme under both pH conditions tested.

The relatively high activities displayed by hybrids G and H are particularly interesting. These hybrids contain residues 215-483 and 246-483 of AmyS, respectively, meaning that they possesses the entire B domain of Ultrathin, as well as a significant portion of the Ultrathin catalytic A domain. If the AmyS variant lacking the 29 amino acid C-terminal starch binding domain were used to contribute the AmyS sequence in hybrid H, about 50% of the residues of this hybrid would be Ultrathin residues. It is expected that these hybrid amylases will not require $Ca^{2+}$, because the calcium binding site of AmyS is completely replaced by the zinc binding site from Ultrathin.

It will be apparent to those skilled in the art that various modifications and variation can be made to the compositions and methods of using the same without departing from the spirit or scope of the intended use herein. Thus, it is the modifications and variations provided they come within the scope of the appended claims and their equivalents.

SEQUENCE LISTING

| SEQUENCE LISTING |
|---|

SEQ ID NO: 1: Hybrid A: AAM48115.1 A1 to I104/AmyS A100 to R483.
Residues 1-488.
1-104 = AAM48115.1 (w/o N-term Met) residues are shown in bold
105-488 = AmyS residues 100-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D V V F D H K G G A D G T E W V D A V E V N P S D R N
Q E I S G T Y Q I Q A W T K F D F P G R G N T Y S S F K W R W Y H
F D G V D W D E S R K L S R I Y K F R G I G K A W D W E V D T E N
G N Y D Y L M Y A D L D M D H P E V V T E L K N W G K W Y V N T T
N I D G F R L D A V K H I K F S F F P D W L S Y V R S Q T G K P L
F T V G E Y W S Y D I N K L H N Y I T K T M S L F D A P L H
N K F Y T A S K S G G A F D M R T L M T N T L M K D Q P T L A V T
F V D N H D T E P G Q A L Q S W V D P W F K P L A Y A F I L T R Q
E G Y P C V F Y G D Y Y G I P Q Y N I P S L K S K I D P L L I A R
R D Y A Y G T Q H D Y L D H S D I I G W T R E G V T E K P G S G L
A A L I T D G P G G S K W M Y V G K Q H A G K V F Y D L T G N R S
D T V T I N S D G W G E F K V N G G S V S V W V P R
```

SEQ ID NO: 2: Hybrid B: AAM48115.1 A1 to A113/AmyS G109 to R483.
Residues 1-488. 1-113 = AAM48115.1 (w/o N-term Met) residues shown in bold
114-488 = AmyS residues 109-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D I V I N H R A G A D G T E W V D A V E V N P S D R N
Q E I S G T Y Q I Q A W T K F D F P G R G N T Y S S F K W R W Y H
F D G V D W D E S R K L S R I Y K F R G I G K A W D W E V D T E N
G N Y D Y L M Y A D L D M D H P E V V T E L K N W G K W Y V N T T
N I D G F R L D A V K H I K F S F F P D W L S Y V R S Q T G K P L
F T V G E Y W S Y D I N K L H N Y I T K T N G T M S L F D A P L H
N K F Y T A S K S G G A F D M R T L M T N T L M K D Q P T L A V T
F V D N H D T E P G Q A L Q S W V D P W F K P L A Y A F I L T R Q
E G Y P C V F Y G D Y Y G I P Q Y N I P S L K S K I D P L L I A R
R D Y A Y G T Q H D Y L D H S D I I G W T R E G V T E K P G S G L
A A L I T D G P G G S K W M Y V G K Q H A G K V F Y D L T G N R S
D T V T I N S D G W G E F K V N G G S V S V W V P R
```

SEQ ID NO: 3: Hybrid C: AAM48115.1 A1 to W128/AmyS T140 to R483.
Residues 1-472.
1-128 = AAM48115.1 (w/o N-term Met) residues are shown in bold
129-472 = AmyS residues 140-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D I V I N H R A G G D L E W N P F V N D Y T W T K F D
F P G R G N T Y S S F K W R W Y H F D G V D W D E S R K L S R I Y
K F R G I G K A W D W E V D T E N G N Y D Y L M Y A D L D M D H P
E V V T E L K N W G K W Y V N T T N I D G F R L D A V K H I K F S
F F P D W L S Y V R S Q T G K P L F T V G E Y W S Y D I N K L H N
Y I T K T N G T M S L F D A P L H N K F Y T A S K S G G A F D M R
T L M T N T L M K D Q P T L A V T F V D N H D T E P G Q A L Q S W
V D P W F K P L A Y A F I L T R Q E G Y P C V F Y G D Y Y G I P Q
Y N I P S L K S K I D P L L I A R R D Y A Y G T Q H D Y L D H S D
I I G W T R E G V T E K P G S G L A A L I T D G P G G S K W M Y V
G K Q H A G K V F Y D L T G N R S D T V T I N S D G W G E F K V N
G G S V S V W V P R
```

SEQ ID NO: 4: Hybrid D: AAM48115.1 A1 to D145/AmyS F161 to R483.
Residues 1-468.
1-145 = AAM48115.1 (w/o N-term Met) residues are shown in bold
146-468 = AmyS residues 161-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D I V I N H R A G G D L E W N P F V N D Y T W T D F S
K V A S G K Y T A N Y L D F D G V D W D E S R K L S R I Y K F R G
I G K A W D W E V D T E N G N Y D Y L M Y A D L D M D H P E V V T
E L K N W G K W Y V N T T N I D G F R L D A V K H I K F S F F P D
W L S Y V R S Q T G K P L F T V G E Y W S Y D I N K L H N Y I T K
T N G T M S L F D A P L H N K F Y T A S K S G G A F D M R T L M T
N T L M K D Q P T L A V T F V D N H D T E P G Q A L Q S W V D P W
F K P L A Y A F I L T R Q E G Y P C V F Y G D Y Y G I P Q Y N I P
S L K S K I D P L L I A R R D Y A Y G T Q H D Y L D H S D I I G W
```

```
T R E G V T E K P G S G L A A L I T D G P G G S K W M Y V G K Q H
A G K V F Y D L T G N R S D T V T I N S D W G E F K V N G G S V
S V W V P R
```

SEQ ID NO: 5: Hybrid E: AAM48115.1 A1 to P163/AmyS D203 to R483
Residues 1-444.
1-163 = AAM48115.1 (w/o N-term Met) residues are shown in bold
164-444 = AmyS residues 203-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D I V I N H R A G G D L E W N P F V N D Y T W T D F S
K V A S G K Y T A N Y L D F H P N E L H A G D S G T F G G Y P D L
D M D H P E V V T E L K N W G K W Y V N T T N I D G F R L D A V K
H I K F S F F P D W L S Y V R S Q T G K P L F T V G E Y W S Y D I
N K L H N Y I T K T N G T M S L F D A P L H N K F Y T A S K S G G
A F D M R T L M T N T L M K D Q P T L A V T F V D N H D T E P G Q
A L Q S W V D P W F K P L A Y A F I L I R Q E G Y P C V F Y G D Y
Y G I P Q Y N I P S L K S K I D P L L I A R R D Y A Y G T Q H D Y
L D H S D I I G W T R E G V T E K P G S G L A A L I T D G P G G S
K W M Y V G K Q H A G K V F Y D L T G N R S D T V T I N S D G W G
E F K V N G G S V S V W V P R
```

SEQ ID NO: 6: Hybrid F: AAM48115.1 A1 to W175/AmyS L215 to R483
Residues 1-444.
1-175 = AAM48115.1 (w/o N-term Met) residues are shown in bold
176-444 = AmyS residues 215-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D I V I N H R A G G D L E W N P F V N D Y T W T D F S
K V A S G K Y T A N Y L D F H P N E L H A G D S G T F G G Y P D I
C H D K S W D Q Y W L K N W G K W Y V N T T N I D G F R L D A V K
H I K F S F F P D W L S Y V R S Q T G K P L F T V G E Y W S Y D I
N K L H N Y I T K T N G T M S L F D A P L H N K F Y T A S K S G G
A F D M R T L M T N T L M K D Q P T L A V T F V D N H D T E P G Q
A L Q S W V D P W F K P L A Y A F I L I R Q E G Y P C V F Y G D Y
Y G I P Q Y N I P S L K S K I D P L L I A R R D Y A Y G T Q H D Y
L D H S D I I G W T R E G V T E K P G S G L A A L I T D G P G G S
K W M Y V G K Q H A G K V F Y D L T G N R S D T V T I N S D G W G
E F K V N G G S V S V W V P R
```

SEQ ID NO: 7: Hybrid G: AAM48115.1 A1 to G191/AmyS I228 to483
Residues 1-447.
1-191 = AAM48115.1 (w/o N-term Met) residues are shown in bold.
192-447 = AmyS residues 228-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D I V I N H R A G G D L E W N P F V N D Y T W T D F S
K V A S G K Y T A N Y L D F H P N E L H A G D S G T F G G Y P D I
C H D K S W D Q Y W L W A S Q E S Y A A Y L R S I G I D G F R L D
A V K H I K F S F F P D W L S Y V R S Q T G K P L F T V G E Y W S
Y D I N K L H N Y I T K T N G T M S L F D A P L H N K F Y T A S K
S G G A F D M R T L M T N T L M K D Q P T L A V T F V D N H D T E
P G Q A L Q S W V D P W F K P L A Y A F I L T R Q E G Y P C V F Y
G D Y Y G I P Q Y N I P S L K S K I D P L L I A R R D Y A Y G T Q
H D Y L D H S D I I G W T R E G V T E K P G S G L A A L I T D G P
G G S K W M Y V G K Q H A G K V F Y D L T G N R S D T V T I N S D
G W G E F K V N G G S V S V W V P R
```

SEQ ID NO: 8: Hybrid H: AAM48115.1 A1 to K209/AmyS A246 to R483
Residues 1-447.
1-209 = AAM48115.1 (w/o N-term Met) residues shown in bold
210-447 = AmyS residues 246-483

```
A K Y S E L E K G G V I M Q A F Y W D V P S G G I W W D T I R Q K
I P E W Y D A G I S A I W I P P A S K G M G G A Y S M G Y D P Y D
F F D L G E Y D Q K G T V E T R F G S K Q E L V N M I N T A H A Y
G M K V I A D I V I N H R A G G D L E W N P F V N D Y T W T D F S
K V A S G K Y T A N Y L D F H P N E L H A G D S G T F G G Y P D I
C H D K S W D Q Y W L W A S Q E S Y A A Y L R S I G I D G W R F D
Y V K G Y A P W V V K D W L S Y V R S Q T G K P L F T V G E Y W S
Y D I N K L H N Y I T K T N G T M S L F D A P L H N K F Y T A S K
S G G A F D M R T L M T N T L M K D Q P T L A V T F V D N H D T E
P G Q A L Q S W V D P W F K P L A Y A F I L T R Q E G Y P C V F Y
G D Y Y G I P Q Y N I P S L K S K I D P L L I A R R D Y A Y G T Q
H D Y L D H S D I I G W T R E G V T E K P G S G L A A L I T D G P
```

```
                    GGSKWMYVGKQHAGKVFYDLTGNRSDTVTINSD
                    GWGEFKVNGGSVSVWVPR

SEQ ID NO: 9: Ultrathin alpha-amylase (Accession Number AAM48115.1)
MAKYSELEKGGVIMQAFYWDVPSGGIWWDTIRQKIPEWYDAGISAIWIPPASKGMGGAYSMGYDP
YDFFDLGEYDQKGTVETRFGSKQELVNMINTAHAYGMKVIADIVINHRAGGDLEWNPFVNDYTWT
DFSKVASGKYTANYLDFHPNELHAGDSGTFGGYPDICHDKSWDQYWLWASQESYAAYLRSIGIDA
WRFDYVKGYAPWVVKDWLNWWGGWAVGEYWDTNVDAVLNWAYSSGAKVFDFALYYKMDEAFDNKN
IPALVSALQNGQTVVSRDPFKAVTFVANHDTDIIWNKYPAYAFILTYEGQPTIFYRDYEEWLNKD
KLKNLIWIHENLAGGSTDIVYYDNDELIFVRNGYGDKPGLITYINLGSSKAGRWVYVPKFAGACI
HEYTGNLGGWVDKYVYSSGWVYLEAPAYDPANGQYGYSVWSYCGVG SEQ ID NO: 10: AmyS, full-length protein sequence (B. stearothermophilus
amylase) (NCBI PDB structure number 1HVX, protein number 1HVX.A)
  1 AAPFNGTMMQ YFEWYLPDDG TLWTKVANEA NNLSSLGMVA LWLPPAYKGT SRSDVGYGVY
 61 DLYDLGEFNQ KGAVRTKYGT KAQYLQAIQA AHAAGMQVYA DVVFDHKGGA DGTEWVDAVE
121 VNPSDRNQEI SGTYQIQAWT KFDFPGRGNT YSSFKWRWYH FDGVDWDESR KLSRIYKFRG
181 IGKAWDWEVD TENGNYDYLM YADLDMDHPE VVTELKSWGK WYVNTTNIDG FRLDAVKHIK
241 FSFFPDWLSY VRSQTGKPLF TVGEYWSYDI NKLHNYIMKT NGTMSLFDAP LHNKFYTASK
301 SGGTFDMRTL MTNTLMKDQP TLAVTFVDNH DTEPGQALQS WVDPWFKPLA YAFILTRQEG
361 YPCVFYGDYY GIPQYNIPSL KSKIDPLLIA RRDYAYGTQH DYLDHSDIIG WTREGVTEKP
421 GSGLAALITD GPGGSKWMYV GKQHAGKVFY DLTGNRSDTV TINSDGWGEF KVNGGSVSVW
481 VPRKTTVSTI AWSITTRPWT DEFVRWTEPR LVAWP SEQ ID NO: 11: AmyS, truncated at the C-terminus (Geobacillus
stearothermophilus amylase) (NCBI PDB structure number 1HVX,
protein number 1HVX.A).
           10         20         30         40         50         60
AAPFNGTMMQ YFEWYLPDDG TLWTKVANEA NNLSSLGITA LWLPPAYKGT SRSDVGYGVY
           70         80         90        100        110        120
DLYDLGEFNQ KGTVRTKYGT KAQYLQAIQA AHAAGMQVYA DVVFDHKGGA DGTEWVDAVE
          130        140        150        160        170        180
VNPSDRNQEI SGTYQIQAWT KFDFPGRGNT YSSFKWRWYH FDGVDWDESR KLSRIYKFRG
          190        200        210        220        230        240
IGKAWDWEVD TENGNYDYLM YADLDMDHPE VVTELKNWGK WYVNTTNIDG FRLDAVKHIK
          250        260        270        280        290        300
FSFFPDWLSY VRSQTGKPLF TVGEYWSYDI NKLHNYITKT NGTMSLFDAP LHNKFYTASK
          310        320        330        340        350        360
SGGAFDMRTL MTNTLMKDQP TLAVTFVDNH DTEPGQALQS WVDPWFKPLA YAFILTRQEG
          370        380        390        400        410        420
YPCVFYGDYY GIPQYNIPSL KSKIDPLLIA RRDYAYGTQH DYLDHSDIIG WTREGVTEKP
          430        440        450        460        470        480
GSGLAALITD GPGGSKWMYV GKQHAGKVFY DLTGNRSDTV TINSDGWGEF KVNGGSVSVW
VPRKTT SEQ ID NO: 12:
Synthetic sequence
ctcagctctgcagctagcgcagcaa SEQ ID NO: 13:
Synthetic sequence
gtgtggaattgtgagcggcca SEQ ID NO: 14:
Synthetic sequence
agcgagagatgatataccta SEQ ID NO: 15:
Synthetic sequence
tttcggcgtgggtatggtggc SEQ ID NO: 16:
Synthetic sequence
ggtggacgccgtcgaagtcaat SEQ ID NO: 17:
Synthetic sequence
cgcacgttaatgaccaatacac SEQ ID NO: 18:
Synthetic sequence
ctcagctctgcagctagcgcagcaa SEQ ID NO: 19:
Synthetic sequence
gacgacgagcgcgcgatcagaag
```

SEQUENCE LISTING

SEQ ID NO: 20: Hybrid A nucleotide sequence: AAM48115.1/AmyS
**GCAAAGTATAGCGAATTGGAGAAAGGGGGAGTTATAATGCAAGCATTTTATTGGGATGTGCCGTC
CGGCGGCATATGGTGGGACACAATCCGTCAGAAAATTCCGGAATGGTACGATGCGGGCATTTCGG
CGATTTGGATACCGCCTGCTTCTAAAGGCATGGGAGGTGCTTACTCAATGGGCTATGACCCATAT
GATTTCTTCGATTTAGGCGAATATGACCAGAAAGGGACAGTCGAGACTCGCTTTGGGTCTAAACA
GGAGTTGGTTAATATGATTAATACCGCGCATGCTTATGGAATGAAAGTGATA**GCCGATGTCGTGT
TCGACCATAAAGGCGGCGCTGACGGCACGGAATGGGTGGACGCCGTCGAAGTCAATCCGTCCGAC
CGCAACCAAGAAATCTCAGGCACCTATCAAATCCAAGCATGGACGAAATTTGATTTTCCCGGGCG
GGGCAACACATACTCTAGCTTTAAGTGGCGCTGGTACCATTTTGACGGCGTTGATTGGGACGAAA
GCCGTAAATTAAGCCGCATTTACAAATTCCGCGGCATCGGCAAAGCGTGGGATTGGGAAGTAGAC
ACAGAAAACGGAAACTATGACTACTTAATGTATGCCGACCTTGATATGGACCATCCGGAAGTCGT
GACCGAGCTCAAAAACTGGGGGAAATGGTATGTCAACACAACGAACATTGATGGGTTCCGGCTTG
ATGCCGTCAAGCATATTAAGTTCAGCTTTTTTCCTGATTGGTTGTCATATGTGCGTTCTCAGACT
GGCAAGCCGCTGTTTACAGTCGGGGAATATTGGAGCTATGATATCAACAAGTTGCACAATTACAT
TACGAAAACAAACGGAACGATGTCTTTGTTTGATGCCCCGTTACACAACAAATTTTATACCGCTT
CCAAAAGCGGGGGCGCATTTGATATGCGCACGTTAATGACCAATACACTGATGAAAGATCAACCG
ACATTGGCCGTCACGTTCGTTGATAATCATGACACAGAGCCGGGCCAAGCGCTTCAGTCATGGGT
CGACCCATGGTTCAAACCGTTGGCTTACGCCTTTATTCTGACACGGCAGGAAGGATACCCGTGCG
TCTTTTATGGTGACTATTATGGCATTCCACAATATAACATTCCTTCTCTGAAAAGCAAAATCGAT
CCGCTTCTGATCGCGCGCCGTGATTATGCTTACGGAACGCAACATGATTATCTTGATCACTCAGA
CATCATTGGGTGGACAAGAGAAGGGGTCACAGAAAAACCAGGATCAGGCCTCGCCGCACTGATCA
CGGATGGGCCGGGAGGAAGCAAATGGATGTACGTTGGCAAACAGCATGCTGGAAAAGTGTTCTAT
GACCTTACAGGCAACCGGAGCGACACAGTCACGATCAACTCAGATGGATGGGGGGAATTCAAAGT
CAATGGCGGTAGCGTTTCAGTTTGGGTTCCTAGA SEQ ID NO: 21: Hybrid B nucleotide sequence
**GCAAAGTATAGCGAATTGGAGAAAGGGGGAGTTATAATGCAAGCATTTTATTGGGATGTGCCGTC
CGGCGGCATATGGTGGGACACAATCCGTCAGAAAATTCCGGAATGGTACGATGCGGGCATTTCGG
CGATTTGGATACCGCCTGCTTCTAAAGGCATGGGAGGTGCTTACTCAATGGGCTATGACCCATAT
GATTTCTTCGATTTAGGCGAATATGACCAGAAAGGGACAGTCGAGACTCGCTTTGGGTCTAAACA
GGAGTTGGTTAATATGATTAATACCGCGCATGCTTATGGAATGAAAGTGATAGCCGATATTGTCA
TCAACCACAGAGCT**GGCGCTGACGGCACGGAATGGGTGGACGCCGTCGAAGTCAATCCGTCCGAC
CGCAACCAAGAAATCTCAGGCACCTATCAAATCCAAGCATGGACGAAATTTGATTTTCCCGGGCG
GGGCAACACATACTCTAGCTTTAAGTGGCGCTGGTACCATTTTGACGGCGTTGATTGGGACGAAA
GCCGTAAATTAAGCCGCATTTACAAATTCCGCGGCATCGGCAAAGCGTGGGATTGGGAAGTAGAC
ACAGAAAACGGAAACTATGACTACTTAATGTATGCCGACCTTGATATGGACCATCCGGAAGTCGT
GACCGAGCTCAAAAACTGGGGGAAATGGTATGTCAACACAACGAACATTGATGGGTTCCGGCTTG
ATGCCGTCAAGCATATTAAGTTCAGCTTTTTTCCTGATTGGTTGTCATATGTGCGTTCTCAGACT
GGCAAGCCGCTGTTTACAGTCGGGGAATATTGGAGCTATGATATCAACAAGTTGCACAATTACAT
TACGAAAACAAACGGAACGATGTCTTTGTTTGATGCCCCGTTACACAACAAATTTTATACCGCTT
CCAAAAGCGGGGGCGCATTTGATATGCGCACGTTAATGACCAATACACTGATGAAAGATCAACCG
ACATTGGCCGTCACGTTCGTTGATAATCATGACACAGAGCCGGGCCAAGCGCTTCAGTCATGGGT
CGACCCATGGTTCAAACCGTTGGCTTACGCCTTTATTCTGACACGGCAGGAAGGATACCCGTGCG
TCTTTTATGGTGACTATTATGGCATTCCACAATATAACATTCCTTCTCTGAAAAGCAAAATCGAT
CCGCTTCTGATCGCGCGCCGTGATTATGCTTACGGAACGCAACATGATTATCTTGATCACTCAGA
CATCATTGGGTGGACAAGAGAAGGGGTCACAGAAAAACCAGGATCAGGCCTCGCCGCACTGATCA
CGGATGGGCCGGGAGGAAGCAAATGGATGTACGTTGGCAAACAGCATGCTGGAAAAGTGTTCTAT
GACCTTACAGGCAACCGGAGCGACACAGTCACGATCAACTCAGATGGATGGGGGGAATTCAAAGT
CAATGGCGGTAGCGTTTCAGTTTGGGTTCCTAGA SEQ ID NO: 22: Hybrid C nucleotide sequence
**GCAAAGTATAGCGAATTGGAGAAAGGGGGAGTTATAATGCAAGCATTTTATTGGGATGTGCCGTC
CGGCGGCATATGGTGGGACACAATCCGTCAGAAAATTCCGGAATGGTACGATGCGGGCATTTCGG
CGATTTGGATACCGCCTGCTTCTAAAGGCATGGGAGGTGCTTACTCAATGGGCTATGACCCATAT
GATTTCTTCGATTTAGGCGAATATGACCAGAAAGGGACAGTCGAGACTCGCTTTGGGTCTAAACA
GGAGTTGGTTAATATGATTAATACCGCGCATGCTTATGGAATGAAAGTGATAGCCGATATTGTCA
TCAACCACAGAGCTGGGGGCGACCTCGAATGGAACCGTTTGTCAACGATTACACTTGGA**CGAAA
TTTGATTTTCCCGGGCGGGGCAACACATACTCTAGCTTTAAGTGGCGCTGGTACCATTTTGACGG
CGTTGATTGGGACGAAAGCCGTAAATTAAGCCGCATTTACAAATTCCGCGGCATCGGCAAAGCGT
GGGATTGGGAAGTAGACACAGAAAACGGAAACTATGACTACTTAATGTATGCCGACCTTGATATG
GACCATCCGGAAGTCGTGACCGAGCTCAAAAACTGGGGGAAATGGTATGTCAACACAACGAACAT
TGATGGGTTCCGGCTTGATGCCGTCAAGCATATTAAGTTCAGCTTTTTTCCTGATTGGTTGTCAT
ATGTGCGTTCTCAGACTGGCAAGCCGCTGTTTACAGTCGGGGAATATTGGAGCTATGATATCAAC
AAGTTGCACAATTACATTACGAAAACAAACGGAACGATGTCTTTGTTTGATGCCCCGTTACACAA
CAAATTTTATACCGCTTCCAAAAGCGGGGGCGCATTTGATATGCGCACGTTAATGACCAATACAC
TGATGAAAGATCAACCGACATTGGCCGTCACGTTCGTTGATAATCATGACACAGAGCCGGGCCAA
GCGCTTCAGTCATGGGTCGACCCATGGTTCAAACCGTTGGCTTACGCCTTTATTCTGACACGGCA
GGAAGGATACCCGTGCGTCTTTTATGGTGACTATTATGGCATTCCACAATATAACATTCCTTCTC
TGAAAAGCAAAATCGATCCGCTTCTGATCGCGCGCCGTGATTATGCTTACGGAACGCAACATGAT
TATCTTGATCACTCAGACATCATTGGGTGGACAAGAGAAGGGGTCACAGAAAAACCAGGATCAGG
CCTCGCCGCACTGATCACGGATGGGCCGGGAGGAAGCAAATGGATGTACGTTGGCAAACAGCATG
CTGGAAAAGTGTTCTATGACCTTACAGGCAACCGGAGCGACACAGTCACGATCAACTCAGATGGA
TGGGGGGAATTCAAAGTCAATGGCGGTAGCGTTTCAGTTTGGGTTCCTAGA

SEQUENCE LISTING

SEQ ID NO: 23: Hybrid D nucleotide sequence
**GCAAAGTATAGCGAATTGGAGAAAGGGGGAGTTATAATGCAGCATTTTATTGGGATGTG
CCGTCCGGCGGCATATGGTGGGACACAATCCGTCAGAAAATTCCGGAATGGTACGATGCG
GGCATTTCGGCGATTTGGATACCGCCTGCTTCTAAAGGCATGGGAGGTGCTTACTCAATG
GGCTATGACCCATATGATTTCTTCGATTTAGGCGAATATGACCAGAAAGGGACAGTCGAG
ACTCGCTTTGGGTCTAAACAGGAGTTGGTTAATATGATTAATACCGCGCATGCTTATGGA
ATGAAAGTGATAGCCGATATTGTCATCAACCACAGAGCTGGGGCGACCTCGAATGGAAC
CCGTTTGTCAACGATTACACTTGGACGGATTTTTCAAAAGTCGCGAGCGGCAAGTATACG
GCTAATTACTTAGAC**TTTGACGGCGTTGATTGGGACGAAAGCCGTAAATTAAGCCGCATT
TACAAATTCCGCGGCATCGGCAAAGCGTGGGATTGGGAAGTAGACACAGAAAACGGAAAC
TATGACTACTTAATGTATGCCGACCTTGATATGGACCATCCGGAAGTCGTGACCGAGCTC
AAAAACTGGGGAAATGGTATGTCAACACAACGAACATTGATGGGTTCCGGCTTGATGCC
GTCAAGCATATTAAGTTCAGCTTTTTTCCTGATTGGTTGTCATATGTGCGTTCTCAGACT
GGCAAGCCGCTGTTTACAGTCGGGGAATATTGGAGCTATGATATCAACAAGTTGCACAAT
TACATTACGAAAACAAACGGAACGATGTCTTTGTTTGATGCCCCGTTACACAACAAATTT
TATACCGCTTCCAAAAGCGGGGGCGCATTTGATATGCGCACGTTAATGACCAATACACTG
ATGAAAGATCAACCGACATTGGCCGTCACGTTCGTTGATAATCATGACACAGAGCCGGGC
CAAGCGCTTCAGTCATGGGTCGACCCATGGTTCAAACCGTTGGCTTACGCCTTTATTCTG
ACACGGCAGGAAGGATACCCGTGCGTCTTTTATGGTGACTATTATGGCATTCCACAATAT
AACATTCCTTCTCTGAAAAGCAAAATCGATCCGCTTCTGATCGCGCGCCGTGATTATGCT
TACGGAACGCAACATGATTATCTTGATCACTCAGACATCATTGGGTGGACAAGAGAAGGG
GTCACAGAAAAACCAGGATCAGGCCTCGCCGCACTGATCACGGATGGGCCGGGAGGAAGC
AAATGGATGTACGTTGGCAAACAGCATGCTGGAAAAGTGTTCTATGACCTTACAGGCAAC
CGGAGCGACACAGTCACGATCAACTCAGATGGATGGGGGGAATTCAAAGTCAATGGCGGT
AGCGTTTCAGTTTGGGTTCCTAGA SEQ ID NO: 24: Hybrid E nucleotide sequence
**GCAAAGTATAGCGAATTGGAGAAAGGGGGAGTTATAATGCAAGCATTTTATTGGGATGTGCCGTC
CGGCGGCATATGGTGGGACACAATCCGTCAGAAAATTCCGGAATGGTACGATGCGGGCATTTCGG
CGATTTGGATACCGCCTGCTTCTAAAGGCATGGGAGGTGCTTACTCAATGGGCTATGACCCATAT
GATTTCTTCGATTTAGGCGAATATGACCAGAAAGGGACAGTCGAGACTCGCTTTGGGTCTAAACA
GGAGTTGGTTAATATGATTAATACCGCGCATGCTTATGGAATGAAAGTGATAGCCGATATTGTCA
TCAACCACAGAGCTGGGGCGACCTCGAATGGAACCCGTTTGTCAACGATTACACTTGGACGGAT
TTTTCAAAAGTCGCGAGCGGCAAGTATACGGCTAATTACTTAGACTTTCACCCAAACGAACTCCA
CGCTGGCGACTCCGGTACATTCGGGGGATATCCT**GACCTTGATATGGACCATCCGGAAGTCGTGA
CCGAGCTCAAAAACTGGGGAAATGGTATGTCAACACAACGAACATTGATGGGTTCCGGCTTGAT
GCCGTCAAGCATATTAAGTTCAGCTTTTTTCCTGATTGGTTGTCATATGTGCGTTCTCAGACTGG
CAAGCCGCTGTTTACAGTCGGGGAATATTGGAGCTATGATATCAACAAGTTGCACAATTACATTA
CGAAAACAAACGGAACGATGTCTTTGTTTGATGCCCCGTTACACAACAAATTTTATACCGCTTCC
AAAAGCGGGGGCGCATTTGATATGCGCACGTTAATGACCAATACACTGATGAAAGATCAACCGAC
ATTGGCCGTCACGTTCGTTGATAATCATGACACAGAGCCGGGCCAAGCGCTTCAGTCATGGGTCG
ACCCATGGTTCAAACCGTTGGCTTACGCCTTTATTCTGACACGGCAGGAAGGATACCCGTGCGTC
TTTTATGGTGACTATTATGGCATTCCACAATATAACATTCCTTCTCTGAAAAGCAAAATCGATCC
GCTTCTGATCGCGCGCCGTGATTATGCTTACGGAACGCAACATGATTATCTTGATCACTCAGACA
TCATTGGGTGGACAAGAGAAGGGGTCACAGAAAAACCAGGATCAGGCCTCGCCGCACTGATCACG
GATGGGCCGGGAGGAAGCAAATGGATGTACGTTGGCAAACAGCATGCTGGAAAAGTGTTCTATGA
CCTTACAGGCAACCGGAGCGACACAGTCACGATCAACTCAGATGGATGGGGGGAATTCAAAGTCA
ATGGCGGTAGCGTTTCAGTTTGGGTTCCTAGA SEQ ID NO: 25: Hybrid F nucleotide sequence
**GCAAAGTATAGCGAATTGGAGAAAGGGGGAGTTATAATGCAAGCATTTTATTGGGATGTGCCGTC
CGGCGGCATATGGTGGGACACAATCCGTCAGAAAATTCCGGAATGGTACGATGCGGGCATTTCGG
CGATTTGGATACCGCCTGCTTCTAAAGGCATGGGAGGTGCTTACTCAATGGGCTATGACCCATAT
GATTTCTTCGATTTAGGCGAATATGACCAGAAAGGGACAGTCGAGACTCGCTTTGGGTCTAAACA
GGAGTTGGTTAATATGATTAATACCGCGCATGCTTATGGAATGAAAGTGATAGCCGATATTGTCA
TCAACCACAGAGCTGGGGCGACCTCGAATGGAACCCGTTTGTCAACGATTACACTTGGACGGAT
TTTTCAAAAGTCGCGAGCGGCAAGTATACGGCTAATTACTTAGACTTTCACCCAAACGAACTCCA
CGCTGGCGACTCCGGTACATTCGGGGGATATCCTGATATCTGTCATGACAAAAGCTGGGATCAAT
ATTGG**CTCAAAAACTGGGGAAATGGTATGTCAACACAACGAACATTGATGGGTTCCGGCTTGAT
GCCGTCAAGCATATTAAGTTCAGCTTTTTTCCTGATTGGTTGTCATATGTGCGTTCTCAGACTGG
CAAGCCGCTGTTTACAGTCGGGGAATATTGGAGCTATGATATCAACAAGTTGCACAATTACATTA
CGAAAACAAACGGAACGATGTCTTTGTTTGATGCCCCGTTACACAACAAATTTTATACCGCTTCC
AAAAGCGGGGGCGCATTTGATATGCGCACGTTAATGACCAATACACTGATGAAAGATCAACCGAC
ATTGGCCGTCACGTTCGTTGATAATCATGACACAGAGCCGGGCCAAGCGCTTCAGTCATGGGTCG
ACCCATGGTTCAAACCGTTGGCTTACGCCTTTATTCTGACACGGCAGGAAGGATACCCGTGCGTC
TTTTATGGTGACTATTATGGCATTCCACAATATAACATTCCTTCTCTGAAAAGCAAAATCGATCC
GCTTCTGATCGCGCGCCGTGATTATGCTTACGGAACGCAACATGATTATCTTGATCACTCAGACA
TCATTGGGTGGACAAGAGAAGGGGTCACAGAAAAACCAGGATCAGGCCTCGCCGCACTGATCACG
GATGGGCCGGGAGGAAGCAAATGGATGTACGTTGGCAAACAGCATGCTGGAAAAGTGTTCTATGA
CCTTACAGGCAACCGGAGCGACACAGTCACGATCAACTCAGATGGATGGGGGGAATTCAAAGTCA
ATGGCGGTAGCGTTTCAGTTTGGGTTCCTAGA SEQ ID NO: 26: Hybrid G nucleotide sequence
**GCAAAGTATAGCGAATTGGAGAAAGGGGGAGTTATAATGCAAGCATTTTATTGGGATGTGCCGTC
CGGCGGCATATGGTGGGACACAATCCGTCAGAAAATTCCGGAATGGTACGATGCGGGCATTTCGG
CGATTTGGATACCGCCTGCTTCTAAAGGCATGGGAGGTGCTTACTCAATGGGCTATGACCCATAT**

-continued

```
GATTTCTTCGATTTAGGCGAATATGACCAGAAAGGGACAGTCGAGACTCGCTTTGGGTCTAAACA
GGAGTTGGTTAATATGATTAATACCGCGCATGCTTATGGAATGAAAGTGATAGCCGATATTGTCA
TCAACCACAGAGCTGGGGGCGACCTCGAATGGAACCCGTTTGTCAACGATTACACTTGGACGGAT
TTTTCAAAAGTCGCGAGCGGCAAGTATACGGCTAATTACTTAGACTTTCACCCAAACGAACTCCA
CGCTGGCGACTCCGGTACATTCGGGGGATATCCTGATATCTGTCATGACAAAAGCTGGGATCAAT
ATTGGCTGTGGGCTTCACAAGAAAGCTACGCCGCATATCTTCGGTCCATCGGGATTGATGGGTTC
CGGCTTGATGCCGTCAAGCATATTAAGTTCAGCTTTTTTCCTGATTGGTTGTCATATGTGCGTTC
TCAGACTGGCAAGCCGCTGTTTACAGTCGGGGAATATTGGAGCTATGATATCAACAAGTTGCACA
ATTACATTACGAAAACAAACGGAACGATGTCTTTGTTTGATGCCCCGTTACACAACAAATTTTAT
ACCGCTTCCAAAAGCGGGGGCGCATTTGATATGCGCACGTTAATGACCAATACACTGATGAAAGA
TCAACCGACATTGGCCGTCACGTTCGTTGATAATCATGACACAGAGCCGGGCCAAGCGCTTCAGT
CATGGGTCGACCCATGGTTCAAACCGTTGGCTTACGCCTTTATTCTGACACGGCAGGAAGGATAC
CCGTGCGTCTTTTATGGTGACTATTATGGCATTCCACAATATAACATTCCTTCTCTGAAAAGCAA
AATCGATCCGCTTCTGATCGCGCGCCGTGATTATGCTTACGGAACGCAACATGATTATCTTGATC
ACTCAGACATCATTGGGTGGACAAGAGAAGGGGTCACAGAAAAACCAGGATCAGGCCTCGCCGCA
CTGATCACGGATGGGCCGGAGGAAGCAAATGGATGTACGTTGGCAAACAGCATGCTGGAAAAGT
GTTCTATGACCTTACAGGCAACCGGAGCGACACAGTCACGATCAACTCAGATGGATGGGGGGAAT
TCAAAGTCAATGGCGGTAGCGTTTCAGTTTGGGTTCCTAGA

SEQ ID NO: 27: Hybrid H nucleotide sequence
GCAAAGTATAGCGAATTGGAGAAAGGGGGAGTTATAATGCAAGCATTTTATTGGGATGTGCCGTC
CGGCGGCATATGGTGGGACACAATCCGTCAGAAAATTCCGGAATGGTACGATGCGGGCATTTCGG
CGATTTGGATACCGCCTGCTTCTAAAGGCATGGGAGGTGCTTACTCAATGGGCTATGACCCATAT
GATTTCTTCGATTTAGGCGAATATGACCAGAAAGGGACAGTCGAGACTCGCTTTGGGTCTAAACA
GGAGTTGGTTAATATGATTAATACCGCGCATGCTTATGGAATGAAAGTGATAGCCGATATTGTCA
TCAACCACAGAGCTGGGGGCGACCTCGAATGGAACCCGTTTGTCAACGATTACACTTGGACGGAT
TTTTCAAAAGTCGCGAGCGGCAAGTATACGGCTAATTACTTAGACTTTCACCCAAACGAACTCCA
CGCTGGCGACTCCGGTACATTCGGGGGATATCCTGATATCTGTCATGACAAAAGCTGGGATCAAT
ATTGGCTGTGGGCTTCACAAGAAAGCTACGCCGCATATCTTCGGTCCATCGGGATCGATGCGTGG
AGGTTTGACTATGTCAAGGGCTATGCTCCTTGGGTTGTCAAAGATTGGTTGTCATATGTGCGTTC
TCAGACTGGCAAGCCGCTGTTTACAGTCGGGGAATATTGGAGCTATGATATCAACAAGTTGCACA
ATTACATTACGAAAACAAACGGAACGATGTCTTTGTTTGATGCCCCGTTACACAACAAATTTTAT
ACCGCTTCCAAAAGCGGGGGCGCATTTGATATGCGCACGTTAATGACCAATACACTGATGAAAGA
TCAACCGACATTGGCCGTCACGTTCGTTGATAATCATGACACAGAGCCGGGCCAAGCGCTTCAGT
CATGGGTCGACCCATGGTTCAAACCGTTGGCTTACGCCTTTATTCTGACACGGCAGGAAGGATAC
CCGTGCGTCTTTTATGGTGACTATTATGGCATTCCACAATATAACATTCCTTCTCTGAAAAGCAA
AATCGATCCGCTTCTGATCGCGCGCCGTGATTATGCTTACGGAACGCAACATGATTATCTTGATC
ACTCAGACATCATTGGGTGGACAAGAGAAGGGGTCACAGAAAAACCAGGATCAGGCCTCGCCGCA
CTGATCACGGATGGGCCGGAGGAAGCAAATGGATGTACGTTGGCAAACAGCATGCTGGAAAAGT
GTTCTATGACCTTACAGGCAACCGGAGCGACACAGTCACGATCAACTCAGATGGATGGGGGGAAT
TCAAAGTCAATGGCGGTAGCGTTTCAGTTTGGGTTCCTAGA
```

What is claimed is:

1. An enzymatically active hybrid α-amylase comprising a polypeptide having, from N-terminus to C-terminus, a first amino acid sequence from an archae α-amylase and a second amino acid sequence from a wild-type Termamyl-like α-amylase or a variant thereof having at least 80% sequence identity to the wild-type Termamyl-like α-amylase;
wherein the first and second amino acid sequences together contain 400 to 500 amino acid residues;
wherein between 30% and 80% of the total amino acids in the hybrid α-amylase are contributed by the archae α-amylase; and
wherein the first amino acid sequence comprises a $Zn^{2+}$ binding site.

2. The enzymatically active hybrid α-amylase of claim 1, wherein the hybrid amylase has an altered level of recombinant expression, solubility, pH activity profile, substrate specificity, or specific activity, compared to the wild-type Termamyl-like α-amylase.

3. The enzymatically active hybrid α-amylase of claim 1, wherein the wild-type Termamyl-like α-amylase is a *Bacillus* α-amylase.

4. The enzymatically active hybrid α-amylase of claim 1, wherein the wild-type Termamyl-like α-amylase is a variant of a *B. stearothermophilus* α-amylase, wherein a starch binding domain is removed from the C-terminus of the *B. stearothermophilus* α-amylase.

5. The enzymatically active hybrid α-amylase of claim 1, wherein the archae α-amylase has the amino acid sequence of SEQ ID NO: 9.

* * * * *

SEQUENCE LISTING

<160> NUMBER OF SEQ ID NOS: 27

<210> SEQ ID NO 1
<211> LENGTH: 488
<212> TYPE: PRT
<213> ORGANISM: Artificial Sequence
<220> FEATURE:
<223> OTHER INFORMATION: Synthetic sequence - Hybrid A: UT 1-104: AmyS
      100-483

<400> SEQUENCE: 1

```
Ala Lys Tyr Ser Glu Leu Glu Lys Gly Gly Val Ile Met Gln Ala Phe
1               5                   10                  15

Tyr Trp Asp Val Pro Ser Gly Gly Ile Trp Trp Asp Thr Ile Arg Gln
            20                  25                  30

Lys Ile Pro Glu Trp Tyr Asp Ala Gly Ile Ser Ala Ile Trp Ile Pro
        35                  40                  45

Pro Ala Ser Lys Gly Met Gly Gly Ala Tyr Ser Met Gly Tyr Asp Pro
    50                  55                  60

Tyr Asp Phe Phe Asp Leu Gly Glu Tyr Asp Gln Lys Gly Thr Val Glu
65                  70                  75                  80

Thr Arg Phe Gly Ser Lys Gln Glu Leu Val Asn Met Ile Asn Thr Ala
                85                  90                  95
```

His Ala Tyr Gly Met Lys Val Ile Ala Asp Val Val Phe Asp His Lys
                100                 105                 110

Gly Gly Ala Asp Gly Thr Glu Trp Val Asp Ala Val Glu Val Asn Pro
            115                 120                 125

Ser Asp Arg Asn Gln Glu Ile Ser Gly Thr Tyr Gln Ile Gln Ala Trp
        130                 135                 140

Thr Lys Phe Asp Phe Pro Gly Arg Gly Asn Thr Tyr Ser Ser Phe Lys
145                 150                 155                 160

Trp Arg Trp Tyr His Phe Asp Gly Val Asp Trp Asp Glu Ser Arg Lys
                165                 170                 175

Leu Ser Arg Ile Tyr Lys Phe Arg Gly Ile Gly Lys Ala Trp Asp Trp
            180                 185                 190

Glu Val Asp Thr Glu Asn Gly Asn Tyr Asp Tyr Leu Met Tyr Ala Asp
        195                 200                 205

Leu Asp Met Asp His Pro Glu Val Val Thr Glu Leu Lys Asn Trp Gly
210                 215                 220

Lys Trp Tyr Val Asn Thr Thr Asn Ile Asp Gly Phe Arg Leu Asp Ala
225                 230                 235                 240

Val Lys His Ile Lys Phe Ser Phe Phe Pro Asp Trp Leu Ser Tyr Val
                245                 250                 255

Arg Ser Gln Thr Gly Lys Pro Leu Phe Thr Val Gly Glu Tyr Trp Ser
            260                 265                 270

Tyr Asp Ile Asn Lys Leu His Asn Tyr Ile Thr Lys Thr Asn Gly Thr
        275                 280                 285

Met Ser Leu Phe Asp Ala Pro Leu His Asn Lys Phe Tyr Thr Ala Ser
        290                 295                 300

Lys Ser Gly Gly Ala Phe Asp Met Arg Thr Leu Met Thr Asn Thr Leu
305                 310                 315                 320

Met Lys Asp Gln Pro Thr Leu Ala Val Thr Phe Val Asp Asn His Asp
                325                 330                 335

Thr Glu Pro Gly Gln Ala Leu Gln Ser Trp Val Asp Pro Trp Phe Lys
            340                 345                 350

Pro Leu Ala Tyr Ala Phe Ile Leu Thr Arg Gln Glu Gly Tyr Pro Cys
        355                 360                 365

Val Phe Tyr Gly Asp Tyr Tyr Gly Ile Pro Gln Tyr Asn Ile Pro Ser
370                 375                 380

Leu Lys Ser Lys Ile Asp Pro Leu Leu Ile Ala Arg Arg Asp Tyr Ala
385                 390                 395                 400

Tyr Gly Thr Gln His Asp Tyr Leu Asp His Ser Asp Ile Ile Gly Trp
                405                 410                 415

Thr Arg Glu Gly Val Thr Glu Lys Pro Gly Ser Gly Leu Ala Ala Leu
            420                 425                 430

Ile Thr Asp Gly Pro Gly Gly Ser Lys Trp Met Tyr Val Gly Lys Gln
        435                 440                 445

His Ala Gly Lys Val Phe Tyr Asp Leu Thr Gly Asn Arg Ser Asp Thr
        450                 455                 460

Val Thr Ile Asn Ser Asp Gly Trp Gly Glu Phe Lys Val Asn Gly Gly
465                 470                 475                 480

Ser Val Ser Val Trp Val Pro Arg
                485

<210> SEQ ID NO 2
<211> LENGTH: 488

<212> TYPE: PRT
<213> ORGANISM: Artificial Sequence
<220> FEATURE:
<223> OTHER INFORMATION: Synthetic sequence - Hybrid B: UT 1-113: AmyS
      109-483

<400> SEQUENCE: 2

```
Ala Lys Tyr Ser Glu Leu Glu Lys Gly Gly Val Ile Met Gln Ala Phe
1               5                   10                  15

Tyr Trp Asp Val Pro Ser Gly Gly Ile Trp Trp Asp Thr Ile Arg Gln
                20                  25                  30

Lys Ile Pro Glu Trp Tyr Asp Ala Gly Ile Ser Ala Ile Trp Ile Pro
            35                  40                  45

Pro Ala Ser Lys Gly Met Gly Gly Ala Tyr Ser Met Gly Tyr Asp Pro
50                  55                  60

Tyr Asp Phe Phe Asp Leu Gly Glu Tyr Asp Gln Lys Gly Thr Val Glu
65                  70                  75                  80

Thr Arg Phe Gly Ser Lys Gln Glu Leu Val Asn Met Ile Asn Thr Ala
                85                  90                  95

His Ala Tyr Gly Met Lys Val Ile Ala Asp Ile Val Ile Asn His Arg
            100                 105                 110

Ala Gly Ala Asp Gly Thr Glu Trp Val Asp Ala Val Glu Val Asn Pro
        115                 120                 125

Ser Asp Arg Asn Gln Glu Ile Ser Gly Thr Tyr Gln Ile Gln Ala Trp
130                 135                 140

Thr Lys Phe Asp Phe Pro Gly Arg Gly Asn Thr Tyr Ser Ser Phe Lys
145                 150                 155                 160

Trp Arg Trp Tyr His Phe Asp Gly Val Asp Trp Asp Glu Ser Arg Lys
                165                 170                 175

Leu Ser Arg Ile Tyr Lys Phe Arg Gly Ile Gly Lys Ala Trp Asp Trp
            180                 185                 190

Glu Val Asp Thr Glu Asn Gly Asn Tyr Asp Tyr Leu Met Tyr Ala Asp
        195                 200                 205

Leu Asp Met Asp His Pro Glu Val Val Thr Glu Leu Lys Asn Trp Gly
210                 215                 220

Lys Trp Tyr Val Asn Thr Thr Asn Ile Asp Gly Phe Arg Leu Asp Ala
225                 230                 235                 240

Val Lys His Ile Lys Phe Ser Phe Phe Pro Asp Trp Leu Ser Tyr Val
                245                 250                 255

Arg Ser Gln Thr Gly Lys Pro Leu Phe Thr Val Gly Glu Tyr Trp Ser
            260                 265                 270

Tyr Asp Ile Asn Lys Leu His Asn Tyr Ile Thr Lys Thr Asn Gly Thr
        275                 280                 285

Met Ser Leu Phe Asp Ala Pro Leu His Asn Lys Phe Tyr Thr Ala Ser
290                 295                 300

Lys Ser Gly Gly Ala Phe Asp Met Arg Thr Leu Met Thr Asn Thr Leu
305                 310                 315                 320

Met Lys Asp Gln Pro Thr Leu Ala Val Thr Phe Val Asp Asn His Asp
                325                 330                 335

Thr Glu Pro Gly Gln Ala Leu Gln Ser Trp Val Asp Pro Trp Phe Lys
            340                 345                 350

Pro Leu Ala Tyr Ala Phe Ile Leu Thr Arg Gln Glu Gly Tyr Pro Cys
        355                 360                 365

Val Phe Tyr Gly Asp Tyr Tyr Gly Ile Pro Gln Tyr Asn Ile Pro Ser
370                 375                 380
```

```
Leu Lys Ser Lys Ile Asp Pro Leu Ile Ala Arg Arg Asp Tyr Ala
385                 390                 395                 400

Tyr Gly Thr Gln His Asp Tyr Leu Asp His Ser Asp Ile Ile Gly Trp
                405                 410                 415

Thr Arg Glu Gly Val Thr Glu Lys Pro Gly Ser Gly Leu Ala Ala Leu
            420                 425                 430

Ile Thr Asp Gly Pro Gly Gly Ser Lys Trp Met Tyr Val Gly Lys Gln
            435                 440                 445

His Ala Gly Lys Val Phe Tyr Asp Leu Thr Gly Asn Arg Ser Asp Thr
        450                 455                 460

Val Thr Ile Asn Ser Asp Gly Trp Gly Glu Phe Lys Val Asn Gly Gly
465                 470                 475                 480

Ser Val Ser Val Trp Val Pro Arg
                485
```

<210> SEQ ID NO 3
<211> LENGTH: 472
<212> TYPE: PRT
<213> ORGANISM: Artificial Sequence
<220> FEATURE:
<223> OTHER INFORMATION: Synthetic sequence - Hybrid C: UT 1-128: AmyS
      140-483

<400> SEQUENCE: 3

```
Ala Lys Tyr Ser Glu Leu Glu Lys Gly Gly Val Ile Met Gln Ala Phe
1               5                   10                  15

Tyr Trp Asp Val Pro Ser Gly Gly Ile Trp Trp Asp Thr Ile Arg Gln
                20                  25                  30

Lys Ile Pro Glu Trp Tyr Asp Ala Gly Ile Ser Ala Ile Trp Ile Pro
            35                  40                  45

Pro Ala Ser Lys Gly Met Gly Gly Ala Tyr Ser Met Gly Tyr Asp Pro
        50                  55                  60

Tyr Asp Phe Phe Asp Leu Gly Glu Tyr Asp Gln Lys Gly Thr Val Glu
65                  70                  75                  80

Thr Arg Phe Gly Ser Lys Gln Glu Leu Val Asn Met Ile Asn Thr Ala
                85                  90                  95

His Ala Tyr Gly Met Lys Val Ile Ala Asp Ile Val Ile Asn His Arg
            100                 105                 110

Ala Gly Gly Asp Leu Glu Trp Asn Pro Phe Val Asn Asp Tyr Thr Trp
        115                 120                 125

Thr Lys Phe Asp Phe Pro Gly Arg Gly Asn Thr Tyr Ser Ser Phe Lys
    130                 135                 140

Trp Arg Trp Tyr His Phe Asp Gly Val Asp Trp Asp Glu Ser Arg Lys
145                 150                 155                 160

Leu Ser Arg Ile Tyr Lys Phe Arg Gly Ile Gly Lys Ala Trp Asp Trp
                165                 170                 175

Glu Val Asp Thr Glu Asn Gly Asn Tyr Asp Tyr Leu Met Tyr Ala Asp
            180                 185                 190

Leu Asp Met Asp His Pro Glu Val Val Thr Glu Leu Lys Asn Trp Gly
        195                 200                 205

Lys Trp Tyr Val Asn Thr Thr Asn Ile Asp Gly Phe Arg Leu Asp Ala
    210                 215                 220

Val Lys His Ile Lys Phe Ser Phe Pro Asp Trp Leu Ser Tyr Val
225                 230                 235                 240

Arg Ser Gln Thr Gly Lys Pro Leu Phe Thr Val Gly Glu Tyr Trp Ser
```

```
                    245                 250                 255
Tyr Asp Ile Asn Lys Leu His Asn Tyr Ile Thr Lys Thr Asn Gly Thr
                260                 265                 270

Met Ser Leu Phe Asp Ala Pro Leu His Asn Lys Phe Tyr Thr Ala Ser
            275                 280                 285

Lys Ser Gly Gly Ala Phe Asp Met Arg Thr Leu Met Thr Asn Thr Leu
        290                 295                 300

Met Lys Asp Gln Pro Thr Leu Ala Val Thr Phe Val Asp Asn His Asp
305                 310                 315                 320

Thr Glu Pro Gly Gln Ala Leu Gln Ser Trp Val Asp Pro Trp Phe Lys
                325                 330                 335

Pro Leu Ala Tyr Ala Phe Ile Leu Thr Arg Gln Glu Gly Tyr Pro Cys
                340                 345                 350

Val Phe Tyr Gly Asp Tyr Tyr Gly Ile Pro Gln Tyr Asn Ile Pro Ser
            355                 360                 365

Leu Lys Ser Lys Ile Asp Pro Leu Leu Ile Ala Arg Arg Asp Tyr Ala
        370                 375                 380

Tyr Gly Thr Gln His Asp Tyr Leu Asp His Ser Asp Ile Ile Gly Trp
385                 390                 395                 400

Thr Arg Glu Gly Val Thr Glu Lys Pro Gly Ser Gly Leu Ala Ala Leu
                405                 410                 415

Ile Thr Asp Gly Pro Gly Gly Ser Lys Trp Met Tyr Val Gly Lys Gln
            420                 425                 430

His Ala Gly Lys Val Phe Tyr Asp Leu Thr Gly Asn Arg Ser Asp Thr
        435                 440                 445

Val Thr Ile Asn Ser Asp Gly Trp Gly Glu Phe Lys Val Asn Gly Gly
    450                 455                 460

Ser Val Ser Val Trp Val Pro Arg
465                 470

<210> SEQ ID NO 4
<211> LENGTH: 468
<212> TYPE: PRT
<213> ORGANISM: Artificial Sequence
<220> FEATURE:
<223> OTHER INFORMATION: Synthetic sequence - Hybrid D: UT 1-145: AmyS
      161-483

<400> SEQUENCE: 4

Ala Lys Tyr Ser Glu Leu Glu Lys Gly Gly Val Ile Met Gln Ala Phe
1               5                   10                  15

Tyr Trp Asp Val Pro Ser Gly Gly Ile Trp Trp Asp Thr Ile Arg Gln
            20                  25                  30

Lys Ile Pro Glu Trp Tyr Asp Ala Gly Ile Ser Ala Ile Trp Ile Pro
        35                  40                  45

Pro Ala Ser Lys Gly Met Gly Gly Ala Tyr Ser Met Gly Tyr Asp Pro
    50                  55                  60

Tyr Asp Phe Phe Asp Leu Gly Glu Tyr Asp Gln Lys Gly Thr Val Glu
65                  70                  75                  80

Thr Arg Phe Gly Ser Lys Gln Glu Leu Val Asn Met Ile Asn Thr Ala
                85                  90                  95

His Ala Tyr Gly Met Lys Val Ile Ala Asp Ile Val Ile Asn His Arg
            100                 105                 110

Ala Gly Gly Asp Leu Glu Trp Asn Pro Phe Val Asn Asp Tyr Thr Trp
        115                 120                 125
```

```
Thr Asp Phe Ser Lys Val Ala Ser Gly Lys Tyr Thr Ala Asn Tyr Leu
130                 135                 140

Asp Phe Asp Gly Val Asp Trp Asp Glu Ser Arg Lys Leu Ser Arg Ile
145                 150                 155                 160

Tyr Lys Phe Arg Gly Ile Gly Lys Ala Trp Asp Trp Glu Val Asp Thr
                165                 170                 175

Glu Asn Gly Asn Tyr Asp Tyr Leu Met Tyr Ala Asp Leu Asp Met Asp
                180                 185                 190

His Pro Glu Val Val Thr Glu Leu Lys Asn Trp Gly Lys Trp Tyr Val
            195                 200                 205

Asn Thr Thr Asn Ile Asp Gly Phe Arg Leu Asp Ala Val Lys His Ile
210                 215                 220

Lys Phe Ser Phe Phe Pro Asp Trp Leu Ser Tyr Val Arg Ser Gln Thr
225                 230                 235                 240

Gly Lys Pro Leu Phe Thr Val Gly Glu Tyr Trp Ser Tyr Asp Ile Asn
                245                 250                 255

Lys Leu His Asn Tyr Ile Thr Lys Thr Asn Gly Thr Met Ser Leu Phe
                260                 265                 270

Asp Ala Pro Leu His Asn Lys Phe Tyr Thr Ala Ser Lys Ser Gly Gly
            275                 280                 285

Ala Phe Asp Met Arg Thr Leu Met Thr Asn Thr Leu Met Lys Asp Gln
290                 295                 300

Pro Thr Leu Ala Val Thr Phe Val Asp Asn His Asp Thr Glu Pro Gly
305                 310                 315                 320

Gln Ala Leu Gln Ser Trp Val Asp Pro Trp Phe Lys Pro Leu Ala Tyr
                325                 330                 335

Ala Phe Ile Leu Thr Arg Gln Glu Gly Tyr Pro Cys Val Phe Tyr Gly
                340                 345                 350

Asp Tyr Tyr Gly Ile Pro Gln Tyr Asn Ile Pro Ser Leu Lys Ser Lys
            355                 360                 365

Ile Asp Pro Leu Leu Ile Ala Arg Arg Asp Tyr Ala Tyr Gly Thr Gln
370                 375                 380

His Asp Tyr Leu Asp His Ser Asp Ile Ile Gly Trp Thr Arg Glu Gly
385                 390                 395                 400

Val Thr Glu Lys Pro Gly Ser Gly Leu Ala Ala Leu Ile Thr Asp Gly
                405                 410                 415

Pro Gly Gly Ser Lys Trp Met Tyr Val Gly Lys Gln His Ala Gly Lys
                420                 425                 430

Val Phe Tyr Asp Leu Thr Gly Asn Arg Ser Asp Thr Val Thr Ile Asn
            435                 440                 445

Ser Asp Gly Trp Gly Glu Phe Lys Val Asn Gly Gly Ser Val Ser Val
    450                 455                 460

Trp Val Pro Arg
465

<210> SEQ ID NO 5
<211> LENGTH: 444
<212> TYPE: PRT
<213> ORGANISM: Artificial Sequence
<220> FEATURE:
<223> OTHER INFORMATION: Synthetic sequence - Hybrid E: UT 1-163: AmyS
      203-483

<400> SEQUENCE: 5

Ala Lys Tyr Ser Glu Leu Glu Lys Gly Gly Val Ile Met Gln Ala Phe
1               5                   10                  15
```

```
Tyr Trp Asp Val Pro Ser Gly Gly Ile Trp Trp Asp Thr Ile Arg Gln
            20                  25                  30

Lys Ile Pro Glu Trp Tyr Asp Ala Gly Ile Ser Ala Ile Trp Ile Pro
            35                  40                  45

Pro Ala Ser Lys Gly Met Gly Gly Ala Tyr Ser Met Gly Tyr Asp Pro
            50                  55                  60

Tyr Asp Phe Phe Asp Leu Gly Glu Tyr Asp Gln Lys Gly Thr Val Glu
 65              70                  75                  80

Thr Arg Phe Gly Ser Lys Gln Glu Leu Val Asn Met Ile Asn Thr Ala
                85                  90                  95

His Ala Tyr Gly Met Lys Val Ile Ala Asp Ile Val Ile Asn His Arg
                100                 105                 110

Ala Gly Gly Asp Leu Glu Trp Asn Pro Phe Val Asn Asp Tyr Thr Trp
                115                 120                 125

Thr Asp Phe Ser Lys Val Ala Ser Gly Lys Tyr Thr Ala Asn Tyr Leu
130                 135                 140

Asp Phe His Pro Asn Glu Leu His Ala Gly Asp Ser Gly Thr Phe Gly
145                 150                 155                 160

Gly Tyr Pro Asp Leu Asp Met Asp His Pro Glu Val Val Thr Glu Leu
                165                 170                 175

Lys Asn Trp Gly Lys Trp Tyr Val Asn Thr Thr Asn Ile Asp Gly Phe
                180                 185                 190

Arg Leu Asp Ala Val Lys His Ile Lys Phe Ser Phe Phe Pro Asp Trp
                195                 200                 205

Leu Ser Tyr Val Arg Ser Gln Thr Gly Lys Pro Leu Phe Thr Val Gly
                210                 215                 220

Glu Tyr Trp Ser Tyr Asp Ile Asn Lys Leu His Asn Tyr Ile Thr Lys
225                 230                 235                 240

Thr Asn Gly Thr Met Ser Leu Phe Asp Ala Pro Leu His Asn Lys Phe
                245                 250                 255

Tyr Thr Ala Ser Lys Ser Gly Gly Ala Phe Asp Met Arg Thr Leu Met
                260                 265                 270

Thr Asn Thr Leu Met Lys Asp Gln Pro Thr Leu Ala Val Thr Phe Val
                275                 280                 285

Asp Asn His Asp Thr Glu Pro Gly Gln Ala Leu Gln Ser Trp Val Asp
                290                 295                 300

Pro Trp Phe Lys Pro Leu Ala Tyr Ala Phe Ile Leu Thr Arg Gln Glu
305                 310                 315                 320

Gly Tyr Pro Cys Val Phe Tyr Gly Asp Tyr Tyr Gly Ile Pro Gln Tyr
                325                 330                 335

Asn Ile Pro Ser Leu Lys Ser Lys Ile Asp Pro Leu Leu Ile Ala Arg
                340                 345                 350

Arg Asp Tyr Ala Tyr Gly Thr Gln His Asp Tyr Leu Asp His Ser Asp
                355                 360                 365

Ile Ile Gly Trp Thr Arg Glu Gly Val Thr Glu Lys Pro Gly Ser Gly
                370                 375                 380

Leu Ala Ala Leu Ile Thr Asp Gly Pro Gly Gly Ser Lys Trp Met Tyr
385                 390                 395                 400

Val Gly Lys Gln His Ala Gly Lys Val Phe Tyr Asp Leu Thr Gly Asn
                405                 410                 415

Arg Ser Asp Thr Val Thr Ile Asn Ser Asp Gly Trp Gly Glu Phe Lys
                420                 425                 430
```

```
Val Asn Gly Gly Ser Val Ser Val Trp Val Pro Arg
            435                 440
```

<210> SEQ ID NO 6
<211> LENGTH: 444
<212> TYPE: PRT
<213> ORGANISM: Artificial Sequence
<220> FEATURE:
<223> OTHER INFORMATION: Synthetic sequence - Hybrid F: UT 1-175: AmyS
      215-483

<400> SEQUENCE: 6

```
Ala Lys Tyr Ser Glu Leu Glu Lys Gly Gly Val Ile Met Gln Ala Phe
1               5                   10                  15

Tyr Trp Asp Val Pro Ser Gly Gly Ile Trp Trp Asp Thr Ile Arg Gln
            20                  25                  30

Lys Ile Pro Glu Trp Tyr Asp Ala Gly Ile Ser Ala Ile Trp Ile Pro
        35                  40                  45

Pro Ala Ser Lys Gly Met Gly Gly Ala Tyr Ser Met Gly Tyr Asp Pro
    50                  55                  60

Tyr Asp Phe Phe Asp Leu Gly Glu Tyr Asp Gln Lys Gly Thr Val Glu
65                  70                  75                  80

Thr Arg Phe Gly Ser Lys Gln Glu Leu Val Asn Met Ile Asn Thr Ala
                85                  90                  95

His Ala Tyr Gly Met Lys Val Ile Ala Asp Ile Val Ile Asn His Arg
            100                 105                 110

Ala Gly Gly Asp Leu Glu Trp Asn Pro Phe Val Asn Asp Tyr Thr Trp
        115                 120                 125

Thr Asp Phe Ser Lys Val Ala Ser Gly Lys Tyr Thr Ala Asn Tyr Leu
    130                 135                 140

Asp Phe His Pro Asn Glu Leu His Ala Gly Asp Ser Gly Thr Phe Gly
145                 150                 155                 160

Gly Tyr Pro Asp Ile Cys His Asp Lys Ser Trp Asp Gln Tyr Trp Leu
                165                 170                 175

Lys Asn Trp Gly Lys Trp Tyr Val Asn Thr Thr Asn Ile Asp Gly Phe
            180                 185                 190

Arg Leu Asp Ala Val Lys His Ile Lys Phe Ser Phe Phe Pro Asp Trp
        195                 200                 205

Leu Ser Tyr Val Arg Ser Gln Thr Gly Lys Pro Leu Phe Thr Val Gly
    210                 215                 220

Glu Tyr Trp Ser Tyr Asp Ile Asn Lys Leu His Asn Tyr Ile Thr Lys
225                 230                 235                 240

Thr Asn Gly Thr Met Ser Leu Phe Asp Ala Pro Leu His Asn Lys Phe
                245                 250                 255

Tyr Thr Ala Ser Lys Ser Gly Gly Ala Phe Asp Met Arg Thr Leu Met
            260                 265                 270

Thr Asn Thr Leu Met Lys Asp Gln Pro Thr Leu Ala Val Thr Phe Val
        275                 280                 285

Asp Asn His Asp Thr Glu Pro Gly Gln Ala Leu Gln Ser Trp Val Asp
    290                 295                 300

Pro Trp Phe Lys Pro Leu Ala Tyr Ala Phe Ile Leu Thr Arg Gln Glu
305                 310                 315                 320

Gly Tyr Pro Cys Val Phe Tyr Gly Asp Tyr Tyr Gly Ile Pro Gln Tyr
                325                 330                 335

Asn Ile Pro Ser Leu Lys Ser Lys Ile Asp Pro Leu Leu Ile Ala Arg
            340                 345                 350
```

```
Arg Asp Tyr Ala Tyr Gly Thr Gln His Asp Tyr Leu Asp His Ser Asp
            355                 360                 365
Ile Ile Gly Trp Thr Arg Glu Gly Val Thr Glu Lys Pro Gly Ser Gly
    370                 375                 380
Leu Ala Ala Leu Ile Thr Asp Gly Pro Gly Gly Ser Lys Trp Met Tyr
385                 390                 395                 400
Val Gly Lys Gln His Ala Gly Lys Val Phe Tyr Asp Leu Thr Gly Asn
                405                 410                 415
Arg Ser Asp Thr Val Thr Ile Asn Ser Asp Gly Trp Gly Glu Phe Lys
            420                 425                 430
Val Asn Gly Gly Ser Val Ser Val Trp Val Pro Arg
            435                 440

<210> SEQ ID NO 7
<211> LENGTH: 447
<212> TYPE: PRT
<213> ORGANISM: Artificial Sequence
<220> FEATURE:
<223> OTHER INFORMATION: Synthetic sequence - Hybrid G: UT 1-191: AmyS
      228-483

<400> SEQUENCE: 7

Ala Lys Tyr Ser Glu Leu Glu Lys Gly Gly Val Ile Met Gln Ala Phe
1               5                   10                  15
Tyr Trp Asp Val Pro Ser Gly Gly Ile Trp Trp Asp Thr Ile Arg Gln
            20                  25                  30
Lys Ile Pro Glu Trp Tyr Asp Ala Gly Ile Ser Ala Ile Trp Ile Pro
        35                  40                  45
Pro Ala Ser Lys Gly Met Gly Gly Ala Tyr Ser Met Gly Tyr Asp Pro
    50                  55                  60
Tyr Asp Phe Phe Asp Leu Gly Glu Tyr Asp Gln Lys Gly Thr Val Glu
65                  70                  75                  80
Thr Arg Phe Gly Ser Lys Gln Glu Leu Val Asn Met Ile Asn Thr Ala
                85                  90                  95
His Ala Tyr Gly Met Lys Val Ile Ala Asp Ile Val Ile Asn His Arg
            100                 105                 110
Ala Gly Gly Asp Leu Glu Trp Asn Pro Phe Val Asn Asp Tyr Thr Trp
        115                 120                 125
Thr Asp Phe Ser Lys Val Ala Ser Gly Lys Tyr Thr Ala Asn Tyr Leu
    130                 135                 140
Asp Phe His Pro Asn Glu Leu His Ala Gly Asp Ser Gly Thr Phe Gly
145                 150                 155                 160
Gly Tyr Pro Asp Ile Cys His Asp Lys Ser Trp Asp Gln Tyr Trp Leu
                165                 170                 175
Trp Ala Ser Gln Glu Ser Tyr Ala Ala Tyr Leu Arg Ser Ile Gly Ile
            180                 185                 190
Asp Gly Phe Arg Leu Asp Ala Val Lys His Ile Lys Phe Ser Phe Phe
        195                 200                 205
Pro Asp Trp Leu Ser Tyr Val Arg Ser Gln Thr Gly Lys Pro Leu Phe
    210                 215                 220
Thr Val Gly Glu Tyr Trp Ser Tyr Asp Ile Asn Lys Leu His Asn Tyr
225                 230                 235                 240
Ile Thr Lys Thr Asn Gly Thr Met Ser Leu Phe Asp Ala Pro Leu His
                245                 250                 255
Asn Lys Phe Tyr Thr Ala Ser Lys Ser Gly Gly Ala Phe Asp Met Arg
```

```
            260                 265                 270
Thr Leu Met Thr Asn Thr Leu Met Lys Asp Gln Pro Thr Leu Ala Val
            275                 280                 285
Thr Phe Val Asp Asn His Asp Thr Glu Pro Gly Gln Ala Leu Gln Ser
            290                 295                 300
Trp Val Asp Pro Trp Phe Lys Pro Leu Ala Tyr Ala Phe Ile Leu Thr
305                 310                 315                 320
Arg Gln Glu Gly Tyr Pro Cys Val Phe Tyr Gly Asp Tyr Tyr Gly Ile
                325                 330                 335
Pro Gln Tyr Asn Ile Pro Ser Leu Lys Ser Lys Ile Asp Pro Leu Leu
            340                 345                 350
Ile Ala Arg Arg Asp Tyr Ala Tyr Gly Thr Gln His Asp Tyr Leu Asp
            355                 360                 365
His Ser Asp Ile Ile Gly Trp Thr Arg Glu Gly Val Thr Glu Lys Pro
            370                 375                 380
Gly Ser Gly Leu Ala Ala Leu Ile Thr Asp Gly Pro Gly Gly Ser Lys
385                 390                 395                 400
Trp Met Tyr Val Gly Lys Gln His Ala Gly Lys Val Phe Tyr Asp Leu
                405                 410                 415
Thr Gly Asn Arg Ser Asp Thr Val Thr Ile Asn Ser Asp Gly Trp Gly
                420                 425                 430
Glu Phe Lys Val Asn Gly Gly Ser Val Ser Val Trp Val Pro Arg
                435                 440                 445

<210> SEQ ID NO 8
<211> LENGTH: 447
<212> TYPE: PRT
<213> ORGANISM: Artificial Sequence
<220> FEATURE:
<223> OTHER INFORMATION: Synthetic sequence - Hybrid H: UT 1-209: AmyS
      246-483

<400> SEQUENCE: 8

Ala Lys Tyr Ser Glu Leu Glu Lys Gly Gly Val Ile Met Gln Ala Phe
1               5                   10                  15
Tyr Trp Asp Val Pro Ser Gly Gly Ile Trp Trp Asp Thr Ile Arg Gln
                20                  25                  30
Lys Ile Pro Glu Trp Tyr Asp Ala Gly Ile Ser Ala Ile Trp Ile Pro
            35                  40                  45
Pro Ala Ser Lys Gly Met Gly Gly Ala Tyr Ser Met Gly Tyr Asp Pro
        50                  55                  60
Tyr Asp Phe Phe Asp Leu Gly Glu Tyr Asp Gln Lys Gly Thr Val Glu
65                  70                  75                  80
Thr Arg Phe Gly Ser Lys Gln Glu Leu Val Asn Met Ile Asn Thr Ala
                85                  90                  95
His Ala Tyr Gly Met Lys Val Ile Ala Asp Ile Val Ile Asn His Arg
            100                 105                 110
Ala Gly Gly Asp Leu Glu Trp Asn Pro Phe Val Asn Asp Tyr Thr Trp
        115                 120                 125
Thr Asp Phe Ser Lys Val Ala Ser Gly Lys Tyr Thr Ala Asn Tyr Leu
    130                 135                 140
Asp Phe His Pro Asn Glu Leu His Ala Gly Asp Ser Gly Thr Phe Gly
145                 150                 155                 160
Gly Tyr Pro Asp Ile Cys His Asp Lys Ser Trp Asp Gln Tyr Trp Leu
                165                 170                 175
```

```
Trp Ala Ser Gln Glu Ser Tyr Ala Ala Tyr Leu Arg Ser Ile Gly Ile
            180                 185                 190

Asp Ala Trp Arg Phe Asp Tyr Val Lys Gly Tyr Ala Pro Trp Val Val
        195                 200                 205

Lys Asp Trp Leu Ser Tyr Val Arg Ser Gln Thr Gly Lys Pro Leu Phe
    210                 215                 220

Thr Val Gly Glu Tyr Trp Ser Tyr Asp Ile Asn Lys Leu His Asn Tyr
225                 230                 235                 240

Ile Thr Lys Thr Asn Gly Thr Met Ser Leu Phe Asp Ala Pro Leu His
                245                 250                 255

Asn Lys Phe Tyr Thr Ala Ser Lys Ser Gly Gly Ala Phe Asp Met Arg
            260                 265                 270

Thr Leu Met Thr Asn Thr Leu Met Lys Asp Gln Pro Thr Leu Ala Val
        275                 280                 285

Thr Phe Val Asp Asn His Asp Thr Glu Pro Gly Gln Ala Leu Gln Ser
    290                 295                 300

Trp Val Asp Pro Trp Phe Lys Pro Leu Ala Tyr Ala Phe Ile Leu Thr
305                 310                 315                 320

Arg Gln Glu Gly Tyr Pro Cys Val Phe Tyr Gly Asp Tyr Tyr Gly Ile
                325                 330                 335

Pro Gln Tyr Asn Ile Pro Ser Leu Lys Ser Lys Ile Asp Pro Leu Leu
            340                 345                 350

Ile Ala Arg Arg Asp Tyr Ala Tyr Gly Thr Gln His Asp Tyr Leu Asp
        355                 360                 365

His Ser Asp Ile Ile Gly Trp Thr Arg Glu Gly Val Thr Glu Lys Pro
    370                 375                 380

Gly Ser Gly Leu Ala Ala Leu Ile Thr Asp Gly Pro Gly Gly Ser Lys
385                 390                 395                 400

Trp Met Tyr Val Gly Lys Gln His Ala Gly Lys Val Phe Tyr Asp Leu
                405                 410                 415

Thr Gly Asn Arg Ser Asp Thr Val Thr Ile Asn Ser Asp Gly Trp Gly
            420                 425                 430

Glu Phe Lys Val Asn Gly Gly Ser Val Ser Val Trp Val Pro Arg
        435                 440                 445

<210> SEQ ID NO 9
<211> LENGTH: 436
<212> TYPE: PRT
<213> ORGANISM: Artificial Sequence
<220> FEATURE:
<223> OTHER INFORMATION: Synthetic sequence - Ultrathin alpha-amylase
      (Accession Number AAM48115.1)

<400> SEQUENCE: 9

Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Trp Asp Thr Ile Arg
                20                  25                  30

Gln Lys Ile Pro Glu Trp Tyr Asp Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95
```

Ala His Ala Tyr Gly Met Lys Val Ile Ala Asp Ile Val Asn His
            100                 105                 110

Arg Ala Gly Gly Asp Leu Glu Trp Asn Pro Phe Val Asn Asp Tyr Thr
            115                 120                 125

Trp Thr Asp Phe Ser Lys Val Ala Ser Gly Lys Tyr Thr Ala Asn Tyr
            130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
            210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 10
<211> LENGTH: 515
<212> TYPE: PRT
<213> ORGANISM: B. stearothermophilus

<400> SEQUENCE: 10

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn

```
                    20                  25                  30
Leu Ser Ser Leu Gly Ile Thr Ala Leu Trp Leu Pro Pro Ala Tyr Lys
            35                  40                  45
Gly Thr Ser Arg Ser Asp Val Gly Tyr Gly Val Tyr Asp Leu Tyr Asp
        50                  55                  60
Leu Gly Glu Phe Asn Gln Lys Gly Ala Val Arg Thr Lys Tyr Gly Thr
65                  70                  75                  80
Lys Ala Gln Tyr Leu Gln Ala Ile Gln Ala His Ala Ala Gly Met
                85                  90                  95
Gln Val Tyr Ala Asp Val Val Phe Asp His Lys Gly Gly Ala Asp Gly
            100                 105                 110
Thr Glu Trp Val Asp Ala Val Glu Val Asn Pro Ser Asp Arg Asn Gln
        115                 120                 125
Glu Ile Ser Gly Thr Tyr Gln Ile Gln Ala Trp Thr Lys Phe Asp Phe
    130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
            180                 185                 190
Asn Gly Asn Tyr Asp Tyr Leu Met Tyr Ala Asp Leu Asp Met Asp His
        195                 200                 205
Pro Glu Val Val Thr Glu Leu Lys Ser Trp Gly Lys Trp Tyr Val Asn
    210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
            260                 265                 270
Leu His Asn Tyr Ile Met Lys Thr Asn Gly Thr Met Ser Leu Phe Asp
        275                 280                 285
Ala Pro Leu His Asn Lys Phe Tyr Thr Ala Ser Lys Ser Gly Gly Thr
    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
        355                 360                 365
Tyr Tyr Gly Ile Pro Gln Tyr Asn Ile Pro Ser Leu Lys Ser Lys Ile
    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
        435                 440                 445
```

```
Phe Tyr Asp Leu Thr Gly Asn Arg Ser Asp Thr Val Thr Ile Asn Ser
            450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Trp Ser Ile Thr Thr
                    485                 490                 495

Arg Pro Trp Thr Asp Glu Phe Val Arg Trp Thr Glu Pro Arg Leu Val
            500                 505                 510

Ala Trp Pro
        515

<210> SEQ ID NO 11
<211> LENGTH: 486
<212> TYPE: PRT
<213> ORGANISM: Geobacillus stearothermophilus

<400> SEQUENCE: 11

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
```

```
            290                 295                 300
Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr
                485

<210> SEQ ID NO 12
<211> LENGTH: 25
<212> TYPE: DNA
<213> ORGANISM: Artificial Sequence
<220> FEATURE:
<223> OTHER INFORMATION: Synthetic sequence

<400> SEQUENCE: 12
ctcagctctg cagctagcgc agcaa                                             25

<210> SEQ ID NO 13
<211> LENGTH: 21
<212> TYPE: DNA
<213> ORGANISM: Artificial Sequence
<220> FEATURE:
<223> OTHER INFORMATION: Synthetic sequence

<400> SEQUENCE: 13
gtgtggaatt gtgagcggcc a                                                 21

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence

<400> SEQUENCE: 14
agcgagagat gatataccta                                                   20

<210> SEQ ID NO 15
<211> LENGTH: 21
<212> TYPE: DNA
<213> ORGANISM: Artificial Sequence
```

<220> FEATURE:
<223> OTHER INFORMATION: Synthetic sequence

<400> SEQUENCE: 15
tttcggcgtg ggtatggtgg c                                           21

<210> SEQ ID NO 16
<211> LENGTH: 22
<212> TYPE: DNA
<213> ORGANISM: Artificial Sequence
<220> FEATURE:
<223> OTHER INFORMATION: Synthetic sequence

<400> SEQUENCE: 16
ggtggacgcc gtcgaagtca at                                          22

<210> SEQ ID NO 17
<211> LENGTH: 22
<212> TYPE: DNA
<213> ORGANISM: Artificial Sequence
<220> FEATURE:
<223> OTHER INFORMATION: Synthetic sequence

<400> SEQUENCE: 17
cgcacgttaa tgaccaatac ac                                          22

<210> SEQ ID NO 18
<211> LENGTH: 25
<212> TYPE: DNA
<213> ORGANISM: Artificial Sequence
<220> FEATURE:
<223> OTHER INFORMATION: Synthetic sequence

<400> SEQUENCE: 18
ctcagctctg cagctagcgc agcaa                                       25

<210> SEQ ID NO 19
<211> LENGTH: 23
<212> TYPE: DNA
<213> ORGANISM: Artificial Sequence
<220> FEATURE:
<223> OTHER INFORMATION: Synthetic sequence

<400> SEQUENCE: 19
gacgacgagc gcgcgatcag aag                                         23

<210> SEQ ID NO 20
<211> LENGTH: 1464
<212> TYPE: DNA
<213> ORGANISM: Artificial  Sequence
<220> FEATURE:
<223> OTHER INFORMATION: Synthetic sequence - Hybrid A nucleotide
      sequence: AAM48115.1/AmyS

<400> SEQUENCE: 20
gcaaagtata gcgaattgga gaaggggga gttataatgc aagcatttta ttgggatgtg      60
ccgtccggcg gcatatggtg ggacacaatc cgtcagaaaa ttccggaatg gtacgatgcg    120
ggcatttcgg cgatttggat accgcctgct tctaaaggca tggaggtgc ttactcaatg    180 ggctatgacc catatgattt cttcgattta ggcgaatatg accagaaagg gacagtcgag    240
actcgctttg gtctaaaaca ggagttggtt aatatgatta ataccgcgca tgcttatgga    300
atgaaagtga tagccgatgt cgtgttcgac cataaaggcg gcgctgacgg cacggaatgg    360
gtggacgccg tcgaagtcaa tccgtccgac cgcaaccaag aaatctcagg cacctatcaa    420

```
atccaagcat ggacgaaatt tgattttccc gggcggggca acacatactc tagctttaag      480
tggcgctggt accattttga cggcgttgat tgggacgaaa gccgtaaatt aagccgcatt      540
tacaaattcc gcggcatcgg caaagcgtgg gattgggaag tagacacaga aaacggaaac      600
tatgactact taatgtatgc cgaccttgat atggaccatc cggaagtcgt gaccgagctc      660
aaaaactggg ggaaatggta tgtcaacaca acgaacattg atgggttccg gcttgatgcc      720
gtcaagcata ttaagttcag cttttttcct gattggttgt catatgtgcg ttctcagact      780
ggcaagccgc tgtttacagt cggggaatat tggagctatg atatcaacaa gttgcacaat      840
tacattacga aaacaaacgg aacgatgtct ttgtttgatg ccccgttaca caacaaattt      900
tataccgctt ccaaaagcgg gggcgcattt gatatgcgca cgttaatgac caatacactg      960
atgaaagatc aaccgacatt ggccgtcacg ttcgttgata atcatgacac agagccgggc     1020
caagcgcttc agtcatgggt cgacccatgg ttcaaaccgt tggcttacgc ctttattctg     1080
acacggcagg aaggataccc gtgcgtcttt tatggtgact attatggcat tccacaatat     1140
aacattcctt ctctgaaaag caaaatcgat ccgcttctga tcgcgcgccg tgattatgct     1200 tacgaacgc aacatgatta tcttgatcac tcagacatca ttgggtggac aagagaaggg     1260
gtcacagaaa aaccaggatc aggcctcgcc gcactgatca cggatgggcc gggaggaagc     1320
aaatggatgt acgttggcaa acagcatgct ggaaaagtgt tctatgacct tacaggcaac     1380
cggagcgaca cagtcacgat caactcagat ggatgggggg aattcaaagt caatggcggt     1440
agcgtttcag tttgggttcc taga                                             1464

<210> SEQ ID NO 21
<211> LENGTH: 1464
<212> TYPE: DNA
<213> ORGANISM: Artificial Sequence
<220> FEATURE:
<223> OTHER INFORMATION: Synthetic sequence - Hybrid B nucleotide
      sequence

<400> SEQUENCE: 21
gcaaagtata gcgaattgga gaaaggggga gttataatgc aagcatttta ttgggatgtg       60
ccgtccggcg gcatatggtg ggacacaatc cgtcagaaaa ttccggaatg gtacgatgcg      120
ggcatttcgg cgatttggat accgcctgct tctaaaggca tgggaggtgc ttactcaatg      180
ggctatgacc catatgattt cttcgattta ggcgaatatg accagaaagg gacagtcgag      240
actcgctttg gtctaaaaca ggagttggtt aatatgatta ataccgcgca tgcttatgga      300
atgaaagtga tagccgatat tgtcatcaac cacagagctg gcgctgacgg cacggaatgg      360
gtggacgccg tcgaagtcaa tccgtccgac cgcaaccaag aaatctcagg cacctatcaa      420
atccaagcat ggacgaaatt tgattttccc gggcggggca acacatactc tagctttaag      480
tggcgctggt accattttga cggcgttgat tgggacgaaa gccgtaaatt aagccgcatt      540
tacaaattcc gcggcatcgg caaagcgtgg gattgggaag tagacacaga aaacggaaac      600
tatgactact taatgtatgc cgaccttgat atggaccatc cggaagtcgt gaccgagctc      660
aaaaactggg ggaaatggta tgtcaacaca acgaacattg atgggttccg gcttgatgcc      720
gtcaagcata ttaagttcag cttttttcct gattggttgt catatgtgcg ttctcagact      780
ggcaagccgc tgtttacagt cggggaatat tggagctatg atatcaacaa gttgcacaat      840
tacattacga aaacaaacgg aacgatgtct ttgtttgatg ccccgttaca caacaaattt      900
tataccgctt ccaaaagcgg gggcgcattt gatatgcgca cgttaatgac caatacactg      960
```

```
atgaaagatc aaccgacatt ggccgtcacg ttcgttgata atcatgacac agagccgggc    1020
caagcgcttc agtcatgggt cgacccatgg ttcaaaccgt tggcttacgc ctttattctg    1080
acacggcagg aaggataccc gtgcgtcttt tatggtgact attatggcat tccacaatat    1140
aacattcctt ctctgaaaag caaaatcgat ccgcttctga tcgcgcgccg tgattatgct    1200
tacggaacgc aacatgatta tcttgatcac tcagacatca ttgggtggac aagagaaggg    1260
gtcacagaaa aaccaggatc aggcctcgcc gcactgatca cggatgggcc gggaggaagc    1320
aaatggatgt acgttggcaa acagcatgct ggaaaagtgt ctatgacct  acaggcaac     1380 cggagcgaca cagtcacgat caactcagat ggatgggggg aattcaaagt caatggcggt    1440
agcgtttcag tttgggttcc taga                                           1464
```

<210> SEQ ID NO 22
<211> LENGTH: 1416
<212> TYPE: DNA
<213> ORGANISM: Artificial Sequence
<220> FEATURE:
<223> OTHER INFORMATION: Synthetic sequence - Hybrid C nucleotide
      sequence

<400> SEQUENCE: 22

```
gcaaagtata gcgaattgga gaaaggggga gttataatgc aagcatttta ttgggatgtg     60
ccgtccggcg gcatatggtg ggacacaatc cgtcagaaaa ttccggaatg gtacgatgcg    120
ggcatttcgg cgatttggat accgcctgct tctaaaggca tgggaggtgc ttactcaatg    180
ggctatgacc catatgattt cttcgattta ggcgaatatg accagaaagg gacagtcgag    240
actcgctttg ggtctaaaca ggagttggtt aatatgatta taccgcgca  tgcttatgga    300 atgaaagtga tagccgatat tgtcatcaac cacagagctg ggggcgaccct cgaatggaac    360 ccgtttgtca cgattacact tggacgaaa  tttgattttc ccgggcgggg caacacatac    420
tctagcttta gtggcgctg  gtaccatttt gacggcgttg attgggacga aagccgtaaa    480
ttaagccgca tttacaaatt ccgcggcatc ggcaaagcgt gggattggga agtagacaca    540
gaaaacggaa actatgacta cttaatgtat gccgaccttg atatggacca tccggaagtc    600
gtgaccgagc tcaaaaactg ggggaaatgg tatgtcaaca caacgaacat tgatgggttc    660
cggcttgatg ccgtcaagca tattaagttc agctttttc  ctgattggtt gtcatatgtg    720
cgttctcaga ctggcaagcc gctgtttaca gtcgggaat  attggagcta tgatatcaac    780
aagttgcaca attacattac gaaaacaaac ggaacgatgt ctttgtttga tgccccgtta    840
cacaacaaat tttataccgc ttccaaaagc gggggcgcat tgatatgcg  cacgttaatg    900 accaatacac tgatgaaaga tcaaccgaca ttggccgtca cgttcgttga taatcatgac    960
acagagccgg ccaagcgct  tcagtcatgg gtcgacccat ggttcaaacc gttggcttac   1020
gcctttattc tgacacggca ggaaggatac ccgtgcgtct ttatggtga  ctattatggc   1080 attccacaat ataacattcc ttctctgaaa agcaaaatcg atccgcttct gatcgcgcgc   1140
cgtgattatg cttacggaac gcaacatgat tatcttgatc actcagacat cattgggtgg   1200
acaagagaag ggtcacaga  aaaaccagga tcaggcctcg ccgcactgat cacggatggg   1260
ccgggaggaa gcaaatggat gtacgttggc aaacagcatg ctggaaaagt gttctatgac   1320
cttacaggca accggagcga cacagtcacg atcaactcag atggatgggg gaattcaaa    1380 gtcaatggcg gtagcgtttc agtttgggtt cctaga                             1416
```

<210> SEQ ID NO 23
<211> LENGTH: 1404
<212> TYPE: DNA
<213> ORGANISM: Artificial Sequence
<220> FEATURE:
<223> OTHER INFORMATION: Synthetic sequence - Hybrid D nucleotide
      sequence

<400> SEQUENCE: 23

| | | | | | |
|---|---|---|---|---|---|
| gcaaagtata | gcgaattgga | gaaaggggga | gttataatgc | aagcatttta | ttgggatgtg | 60 |
| ccgtccggcg | gcatatggtg | ggacacaatc | cgtcagaaaa | ttccggaatg | gtacgatgcg | 120 |
| ggcatttcgg | cgatttggat | accgcctgct | tctaaaggca | tgggaggtgc | ttactcaatg | 180 |
| ggctatgacc | catatgattt | cttcgattta | ggcgaatatg | accagaaagg | gacagtcgag | 240 |
| actcgctttg | ggtctaaaca | ggagttggtt | aatatgatta | ataccgcgca | tgcttatgga | 300 |
| atgaaagtga | tagccgatat | tgtcatcaac | cacagagctg | ggggcgacct | cgaatggaac | 360 |
| ccgtttgtca | acgattacac | ttggacggat | ttttcaaaag | tcgcgagcgg | caagtatacg | 420 |
| gctaattact | tagactttga | cggcgttgat | tgggacgaaa | gccgtaaatt | aagccgcatt | 480 |
| tacaaattcc | gcggcatcgg | caaagcgtgg | gattgggaag | tagacacaga | aaacggaaac | 540 |
| tatgactact | taatgtatgc | cgaccttgat | atggaccatc | cggaagtcgt | gaccgagctc | 600 |
| aaaaactggg | ggaaatggta | tgtcaacaca | acgaacattg | atgggttccg | gcttgatgcc | 660 |
| gtcaagcata | ttaagttcag | cttttttcct | gattggttgt | catatgtgcg | ttctcagact | 720 |
| ggcaagccgc | tgtttacagt | cggggaatat | tggagctatg | atatcaacaa | gttgcacaat | 780 |
| tacattacga | aaacaaacgg | aacgatgtct | ttgtttgatg | ccccgttaca | caacaaattt | 840 |
| tataccgctt | ccaaaagcgg | gggcgcattt | gatatgcgca | cgttaatgac | caatacactg | 900 |
| atgaaagatc | aaccgacatt | ggccgtcacg | ttcgttgata | atcatgacac | agagccgggc | 960 |
| caagcgcttc | agtcatgggt | cgacccatgg | ttcaaaccgt | tggcttacgc | ctttattctg | 1020 |
| acacggcagg | aaggataccc | gtgcgtcttt | tatggtgact | attatggcat | tccacaatat | 1080 |
| aacattcctt | ctctgaaaag | caaaatcgat | ccgcttctga | tcgcgcgccg | tgattatgct | 1140 |
| tacggaacgc | aacatgatta | tcttgatcac | tcagacatca | ttgggtggac | aagagaaggg | 1200 |
| gtcacagaaa | aaccaggatc | aggcctcgcc | gcactgatca | cggatgggcc | gggaggaagc | 1260 |
| aaatggatgt | acgttggcaa | acagcatgct | ggaaaagtgt | tctatgacct | tacaggcaac | 1320 |
| cggagcgaca | cagtcacgat | caactcagat | ggatgggggg | aattcaaagt | caatggcggt | 1380 |
| agcgtttcag | tttgggttcc | taga | | | | 1404 |

<210> SEQ ID NO 24
<211> LENGTH: 1332
<212> TYPE: DNA
<213> ORGANISM: Artificial Sequence
<220> FEATURE:
<223> OTHER INFORMATION: Synthetic sequence - Hybrid E nucleotide
      sequence

<400> SEQUENCE: 24

| | | | | | |
|---|---|---|---|---|---|
| gcaaagtata | gcgaattgga | gaaaggggga | gttataatgc | aagcatttta | ttgggatgtg | 60 |
| ccgtccggcg | gcatatggtg | ggacacaatc | cgtcagaaaa | ttccggaatg | gtacgatgcg | 120 |
| ggcatttcgg | cgatttggat | accgcctgct | tctaaaggca | tgggaggtgc | ttactcaatg | 180 |
| ggctatgacc | catatgattt | cttcgattta | ggcgaatatg | accagaaagg | gacagtcgag | 240 |
| actcgctttg | ggtctaaaca | ggagttggtt | aatatgatta | ataccgcgca | tgcttatgga | 300 |

```
atgaaagtga tagccgatat tgtcatcaac cacagagctg ggggcgacct cgaatggaac    360
ccgtttgtca acgattacac ttggacggat ttttcaaaag tcgcgagcgg caagtatacg    420
gctaattact tagactttca cccaaacgaa ctccacgctg gcgactccgg tacattcggg    480
ggatatcctg accttgatat ggaccatccg gaagtcgtga ccgagctcaa aaactggggg    540
aaatggtatg tcaacacaac gaacattgat gggttccggc ttgatgccgt caagcatatt    600
aagttcagct ttttcctga ttggttgtca tatgtgcgtt ctcagactgg caagccgctg    660
tttacagtcg gggaatattg gagctatgat atcaacaagt tgcacaatta cattacgaaa    720
acaaacggaa cgatgtcttt gtttgatgcc ccgttacaca acaaatttta taccgcttcc    780
aaaagcgggg gcgcatttga tatgcgcacg ttaatgacca atacactgat gaaagatcaa    840
ccgacattgg ccgtcacgtt cgttgataat catgacacag agccgggcca agcgcttcag    900
tcatgggtcg acccatggtt caaaccgttg gcttacgcct ttattctgac acggcaggaa    960
ggatacccgt gcgtctttta tggtgactat tatggcattc cacaatataa cattccttct   1020
ctgaaaagca aaatcgatcc gcttctgatc gcgcgccgtg attatgctta cggaacgcaa   1080
catgattatc ttgatcactc agacatcatt gggtggacaa gagaagggt cacagaaaaa   1140 ccaggatcag gcctcgccgc actgatcacg gatgggccgg gaggaagcaa atggatgtac   1200
gttggcaaac agcatgctgg aaaagtgttc tatgacctta caggcaaccg gagcgacaca   1260
gtcacgatca actcagatgg atgggggga ttcaaagtca atggcggtag cgtttcagtt   1320
tgggttccta ga                                                        1332
```

<210> SEQ ID NO 25
<211> LENGTH: 1332
<212> TYPE: DNA
<213> ORGANISM: Artificial Sequence
<220> FEATURE:
<223> OTHER INFORMATION: Synthetic sequence - Hybrid F nucleotide
      sequence

<400> SEQUENCE: 25

```
gcaaagtata gcgaattgga gaaaggggga gttataatgc aagcatttta ttgggatgtg     60
ccgtccggcg gcatatggtg ggacacaatc cgtcagaaaa ttccggaatg gtacgatgcg    120
ggcatttcgg cgatttggat accgcctgct tctaaaggca tgggaggtgc ttactcaatg    180
ggctatgacc catatgattt cttcgattta ggcgaatatg accagaaagg gacagtcgag    240
actcgctttg gtctaaaaca ggagttggtt aatatgatta taccgcgca tgcttatgga    300 atgaaagtga tagccgatat tgtcatcaac cacagagctg ggggcgacct cgaatggaac    360
ccgtttgtca acgattacac ttggacggat ttttcaaaag tcgcgagcgg caagtatacg    420
gctaattact tagactttca cccaaacgaa ctccacgctg gcgactccgg tacattcggg    480
ggatatcctg atatctgtca tgacaaaagc tgggatcaat attggctcaa aaactggggg    540
aaatggtatg tcaacacaac gaacattgat gggttccggc ttgatgccgt caagcatatt    600
aagttcagct ttttcctga ttggttgtca tatgtgcgtt ctcagactgg caagccgctg    660
tttacagtcg gggaatattg gagctatgat atcaacaagt tgcacaatta cattacgaaa    720
acaaacggaa cgatgtcttt gtttgatgcc ccgttacaca acaaatttta taccgcttcc    780
aaaagcgggg gcgcatttga tatgcgcacg ttaatgacca atacactgat gaaagatcaa    840
ccgacattgg ccgtcacgtt cgttgataat catgacacag agccgggcca agcgcttcag    900
tcatgggtcg acccatggtt caaaccgttg gcttacgcct ttattctgac acggcaggaa    960
```

| | |
|---|---|
| ggatacccgt gcgtctttta tggtgactat tatggcattc cacaatataa cattccttct | 1020 |
| ctgaaaagca aaatcgatcc gcttctgatc gcgcgccgtg attatgctta cggaacgcaa | 1080 |
| catgattatc ttgatcactc agacatcatt gggtggacaa gagaagggt cacagaaaaa | 1140 |
| ccaggatcag gcctcgccgc actgatcacg gatgggccgg gaggaagcaa atggatgtac | 1200 |
| gttggcaaac agcatgctgg aaaagtgttc tatgacctta caggcaaccg gagcgacaca | 1260 |
| gtcacgatca actcgatgg atgggggaa ttcaaagtca atggcggtag cgtttcagtt | 1320 |
| tgggttccta ga | 1332 |

<210> SEQ ID NO 26
<211> LENGTH: 1341
<212> TYPE: DNA
<213> ORGANISM: Artificial Sequence
<220> FEATURE:
<223> OTHER INFORMATION: Synthetic sequence - Hybrid G nucleotide sequence

<400> SEQUENCE: 26

| | |
|---|---|
| gcaaagtata gcgaattgga gaagggggga gttataatgc aagcatttta ttgggatgtg | 60 |
| ccgtccggcg gcatatggtg ggacacaatc cgtcagaaaa ttccggaatg gtacgatgcg | 120 |
| ggcatttcgg cgatttggat accgcctgct tctaaaggca tgggaggtgc ttactcaatg | 180 |
| ggctatgacc catatgattt cttcgattta ggcgaatatg accagaaagg gacagtcgag | 240 |
| actcgctttg ggtctaaaca ggagttggtt aatatgatta ataccgcgca tgcttatgga | 300 |
| atgaaagtga tagccgatat tgtcatcaac cacagagctg ggggcgacct cgaatggaac | 360 |
| ccgtttgtca acgattacac ttggacggat ttttcaaaag tcgcgagcgg caagtatacg | 420 |
| gctaattact tagactttca cccaaacgaa ctccacgctg gcgactccgg tacattcggg | 480 |
| ggatatcctg atatctgtca tgacaaaagc tgggatcaat attggctgtg gcttcacaa | 540 |
| gaaagctacg ccgcatatct tcggtccatc gggattgatg ggttccggct tgatgccgtc | 600 |
| aagcatatta agttcagctt ttttcctgat tggttgtcat atgtgcgttc tcagactggc | 660 |
| aagccgctgt ttacagtcgg ggaatattgg agctatgata tcaacaagtt gcacaattac | 720 |
| attacgaaaa caaacggaac gatgtctttg tttgatgccc cgttacacaa caaattttat | 780 |
| accgcttcca aaagcggggg cgcatttgat atgcgcacgt taatgaccaa tacactgatg | 840 |
| aaagatcaac cgacattggc cgtcacgttc gttgataatc atgacacaga gccgggccaa | 900 |
| gcgcttcagt catgggtcga cccatggttc aaaccgttgg cttacgcctt tattctgaca | 960 |
| cggcaggaag gataccccgtg cgtctttat ggtgactatt atggcattcc acaatataac | 1020 |
| attccttctc tgaaaagcaa aatcgatccg cttctgatcg cgcgccgtga ttatgcttac | 1080 |
| ggaacgcaac atgattatct tgatcactca gacatcattg ggtggacaag agaagggtc | 1140 |
| acagaaaaac caggatcagg cctcgccgca ctgatcacgg atgggccggg aggaagcaaa | 1200 |
| tggatgtacg ttggcaaaca gcatgctgga aaagtgttct atgacttac aggcaaccgg | 1260 |
| agcgacacag tcacgatcaa ctcagatgga tgggggaat tcaaagtcaa tggcggtagc | 1320 |
| gtttcagttt gggttcctag a | 1341 |

<210> SEQ ID NO 27
<211> LENGTH: 1341
<212> TYPE: DNA
<213> ORGANISM: Artificial Sequence
<220> FEATURE:
<223> OTHER INFORMATION: Synthetic sequence - Hybrid H nucleotide sequence

```
<400> SEQUENCE: 27
gcaaagtata gcgaattgga gaaaggggga gttataatgc aagcatttta ttgggatgtg      60
ccgtccggcg gcatatggtg ggacacaatc cgtcagaaaa ttccggaatg gtacgatgcg     120
ggcatttcgg cgatttggat accgcctgct tctaaaggca tggaggtgc ttactcaatg      180 ggctatgacc catatgattt cttcgattta ggcgaatatg accagaaagg gacagtcgag     240
actcgctttg ggtctaaaca ggagttggtt aatatgatta ataccgcgca tgcttatgga     300
atgaaagtga tagccgatat tgtcatcaac cacagagctg ggggcgacct cgaatggaac     360
ccgtttgtca acgattacac ttggacggat ttttcaaaag tcgcgagcgg caagtatacg     420
gctaattact tagactttca cccaaacgaa ctccacgctg gcgactccgg tacattcggg     480
ggatatcctg atatctgtca tgacaaaagc tgggatcaat attggctgtg ggcttcacaa     540
gaaagctacg ccgcatatct tcggtccatc gggatcgatg cgtggaggtt tgactatgtc     600
aagggctatg ctccttgggt tgtcaaagat tggttgtcat atgtgcgttc tcagactggc     660
aagccgctgt ttacagtcgg ggaatattgg agctatgata tcaacaagtt gcacaattac     720
attacgaaaa caaacggaac gatgtctttg tttgatgccc cgttacacaa caaattttat     780
accgcttcca aaagcggggg cgcatttgat atgcgcacgt taatgaccaa tacactgatg     840
aaagatcaac cgacattggc cgtcacgttc gttgataatc atgacacaga gccgggccaa     900
gcgcttcagt catgggtcga cccatggttc aaaccgttgg cttacgcctt tattctgaca     960
cggcaggaag gataccccgtg cgtcttttat ggtgactatt atggcattcc acaatataac    1020
attccttctc tgaaaagcaa aatcgatccg cttctgatcg cgcgccgtga ttatgcttac    1080
ggaacgcaac atgattatct tgatcactca gacatcattg ggtggacaag agaaggggtc    1140
acagaaaaac caggatcagg cctcgccgca ctgatcacgg atgggccggg aggaagcaaa    1200
tggatgtacg ttggcaaaca gcatgctgga aaagtgttct atgaccttac aggcaaccgg    1260
agcgacacag tcacgatcaa ctcagatgga tgggggaat tcaaagtcaa tggcggtagc    1320
gtttcagttt gggttcctag a                                               1341
```